(12) United States Patent
Smith et al.

(10) Patent No.: US 11,788,965 B2
(45) Date of Patent: Oct. 17, 2023

(54) FOLIC ACID FUNCTIONALIZED COPPER SULFIDE NANOPARTICLES FOR THE DETECTION OF OVARIAN CANCER CELLS IN FLOW

(71) Applicants: Barbara Smith, Scottsdale, AZ (US); Joel Lusk, Mesa, AZ (US)

(72) Inventors: Barbara Smith, Scottsdale, AZ (US); Joel Lusk, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 790 days.

(21) Appl. No.: 16/798,038

(22) Filed: Feb. 21, 2020

(65) Prior Publication Data

US 2020/0271655 A1 Aug. 27, 2020

Related U.S. Application Data

(60) Provisional application No. 62/808,442, filed on Feb. 21, 2019.

(51) Int. Cl.
| | |
|---|---|
| *G01N 21/64* | (2006.01) |
| *G01N 15/14* | (2006.01) |
| *G02B 21/00* | (2006.01) |
| *G01N 21/17* | (2006.01) |
| *G01N 33/58* | (2006.01) |

(52) U.S. Cl.
CPC ......... *G01N 21/6458* (2013.01); *G01N 15/14* (2013.01); *G01N 21/6402* (2013.01); *G01N 21/1702* (2013.01); *G01N 33/582* (2013.01); *G01N 2800/56* (2013.01); *G02B 21/0076* (2013.01)

(58) Field of Classification Search
None
See application file for complete search history.

(56) References Cited

U.S. PATENT DOCUMENTS

| 6,108,096 A | * | 8/2000 | Ushio | G01N 21/1702 |
| | | | | 356/440 |
| 8,293,176 B2 | * | 10/2012 | Viator | G01N 21/1702 |
| | | | | 73/861.26 |
| 9,151,709 B2 | * | 10/2015 | O'Brien | G01N 21/1702 |
| 2005/0160800 A1 | * | 7/2005 | Schindler | G01N 29/046 |
| | | | | 73/61.71 |
| 2005/0175540 A1 | * | 8/2005 | Oraevsky | A61B 5/415 |
| | | | | 424/9.5 |

(Continued)

FOREIGN PATENT DOCUMENTS

WO WO-2011068764 A2 * 6/2011 ......... G01N 15/1404

OTHER PUBLICATIONS

Galanzha, Ekaterina I et al. "Nanotechnology-based molecular photoacoustic and photothermal flow cytometry platform for in-vivo detection and killing of circulating cancer stem cells." Journal of biophotonics vol. 2,12 (2009): 725-35. doi:10.1002/jbio. 200910078 (Year: 2009).*

(Continued)

*Primary Examiner* — Ellen J Marcsisin
(74) *Attorney, Agent, or Firm* — Michael Best & Friedrich LLP

(57) ABSTRACT

The disclosure provides a system, compositions, and methods for detecting ovarian cancer cells by photoacoustic flow cytometry.

24 Claims, 28 Drawing Sheets

(56) References Cited

U.S. PATENT DOCUMENTS

| | | | | |
|---|---|---|---|---|
| 2009/0156932 | A1* | 6/2009 | Zharov | A61B 5/412 600/437 |
| 2011/0104069 | A1* | 5/2011 | Xu | A61K 47/6913 424/490 |
| 2014/0147860 | A1* | 5/2014 | Kaduchak | G01N 33/56966 435/7.21 |
| 2015/0351640 | A1* | 12/2015 | Zharov | A61B 5/418 600/407 |
| 2017/0367682 | A1 | 12/2017 | Smith et al. | |
| 2019/0046159 | A1 | 2/2019 | Smith et al. | |
| 2019/0110691 | A1 | 4/2019 | Smith et al. | |
| 2019/0282069 | A1 | 9/2019 | Smith et al. | |
| 2020/0340954 | A1 | 10/2020 | Smith et al. | |

OTHER PUBLICATIONS

Galanzha, Ekaterina I, and Vladimir P Zharov. "Circulating Tumor Cell Detection and Capture by Photoacoustic Flow Cytometry in Vivo and ex Vivo." Cancers vol. 5,4 1691-738. Dec. 10, 2013, doi:10.3390/cancers5041691 (Year: 2013).*
Chinen, Alyssa B et al. "Nanoparticle Probes for the Detection of Cancer Biomarkers, Cells, and Tissues by Fluorescence." Chemical reviews vol. 115,19 (2015): 10530-74. doi:10.1021/acs.chemrev. 5b00321 (Year: 2015).*
Lou, Emil et al. "Assessment of Circulating Tumor Cells as a Predictive Biomarker of Histology in Women With Suspected Ovarian Cancer." Laboratory medicine vol. 49,2 (2018): 134-139. doi:10.1093/labmed/lmx084 (Year: 2018).*
Ovejero, Jesus G et al. "Synthesis of hybrid magneto-plasmonic nanoparticles with potential use in photoacoustic detection of circulating tumor cells." Mikrochimica acta vol. 185,2 130. Jan. 25, 2018, doi:10.1007/s00604-017-2637-x (Year: 2018).*
National Center for Biotechnology Information. "PubChem Compound Summary for CID 135398658, Folic acid" PubChem, https://pubchem.ncbi.nlm.nih.gov/compound/Folic-acid. Accessed Oct. 5, 2022. (Year: 2019).*
Gnyawali et al., Simultaneous acoustic and photoacoustic microfluidic flow cytometry for label-free analysis, Scientific Reports, 9(1585), (2019) (11 pages) (Year: 2019).*
Aguirre et al., "Potential role of coregistered photoacoustic and ultrasound imaging in ovarian cancer detection and characterization." Translational oncology 4.1 (2011): 29-37.
Allard et al., "Tumor cells circulate in the peripheral blood of all major carcinomas but not in healthy subjects or patients with nonmalignant diseases," Clinical cancer research 10(20), 6897-6904 (2004).
Armstrong, "Relapsed ovarian cancer: challenges and management strategies for a chronic disease," The oncologist 7 (Supplement 5), 20-28 (2002).
Balavandy et al. "Stirring time effect of silver nanoparticles prepared in glutathione mediated by green method." Chemistry Central Journal 8.1 (2014): 11.
Bhagwat et al., "An integrated flow cytometry-based platform for isolation and molecular characterization of circulating tumor single cells and clusters," Scientific reports 8(1), 5035 (2018).
Bhattacharyya et al., "Detection and capture of breast cancer cells with photoacoustic flow cytometry," Journal of biomedical optics 21(8), 087007 (2016).
Blassl et al., "Gene expression profiling of single circulating tumor cells in ovarian cancer-establishment of a multi-marker gene panel," Molecular oncology 10(7), 1030-1042 (2016).
Bytesizescience, "The Electronic Nose: Sniffing Out the Dangerous Stuff to Keep Our Noses Safe," <https://www.youtube.com/watch?v=UzIHJOFcCwc> dated May 9, 2012.
Cai et al., "Photoacoustic flow cytometry for single sickle cell detection in vitro and in vivo," Analytical Cellular Pathology 2016 (2016).

Daskalaki et al., "Detection of cytokeratin-19 mrna-positive cells in the peripheral blood and bone marrow of patients with operable breast cancer," British journal of cancer 101(4), 589 (2009).
De Albuquerque et al., "Multimarker analysis of circulating tumor cells in peripheral blood of metastatic breast cancer patients: A step forward in personalized medicine," Breast Care 7(1), 7-12 (2012).
Fan et al., "Clinical significance of circulating tumor cells detected by an invasion assay in peripheral blood of patients with ovarian cancer," Gynecologic oncology 112(1), 185-191 (2009).
Galanzha et al., "In vivo magnetic enrichment and multiplex photoacoustic detection of circulating tumour cells," Nature nanotechnology 4(12), 855 (2009).
Galanzha et al., "Photoacoustic flow cytometry," Methods 57(3), 280-296 (2012).
Gao et al., "Near-infrared fluorescence imaging of cancer cells and tumors through specific biosynthesis of silver nanoclusters." Scientific reports 4 (2014): 4384.
Gorges et al., "Circulating tumour cells escape from epcambased detection due to epithelial-to-mesenchymal transition," BMC cancer 12(1), 178 (2012).
Guo et al., "A comparative study of hollow copper sulfide nanoparticles and hollow gold nanospheres on degradability and toxicity," ACS nano 7(10), 8780-8793 (2013).
He et al., "Quantitation of circulating tumor cells in blood samples from ovarian and prostate cancer patients using tumor-specific fluorescent ligands," International journal of cancer 123(8), 1968-1973 (2008).
Jacobs et al., "Progress and challenges in screening for early detection of ovarian cancer," Molecular & Cellular Proteomics 3(4), 355-366 (2004).
Jelovac et al., "Recent progress in the diagnosis and treatment of ovarian cancer," CA: a cancer journal for clinicians 61(3), 183-203 (2011).
Jiang et al., "An integrated microfluidic device for rapid and highsensitivity analysis of circulating tumor cells," Scientific Reports 7, 42612 (2017).
Khoury-Collado et al., "Recent surgical management of ovarian cancer," Journal of Obstetrics and Gynaecology Research 37(5), 379-382 (2011).
Kipps et al., "Meeting the challenge of ascites in ovarian cancer: new avenues for therapy and research," Nature Reviews Cancer 13(4), 273 (2013).
Ku et al., "Copper sulfide nanoparticles as a new class of photoacoustic contrast agent for deep tissue imaging at 1064 nm," Acs Nano 6(8), 7489-7496 (2012).
Laufer et al., "In vivo preclinical photoacoustic imaging of tumor vasculature development and therapy," J Biomed Opt, 2012, 17(5):056016.
Lee et al., "Predictive value of circulating tumor cells (ctcs) captured by microfluidic device in patients with epithelial ovarian cancer," Gynecologic oncology 145(2), 361-365 (2017).
Liu et al., "Folate-receptor-targeted laser-activable poly (lactidecoglycolic acid) nanoparticles loaded with paclitaxel/ indocyanine green for photoacoustic/ultrasound imaging and chemo/photothermal therapy," International Journal of Nanomedicine 13, 5139 (2018).
Lu et al., "Isolation and characterization of living circulating tumor cells in patients by immunomagnetic negative enrichment coupled with flow cytometry," Cancer 121(17), 3036-3045 (2015).
Lusk et al., "Photoacoustic Flow System for the Detection of Ovarian Circulating Tumor Cells Utilizing Copper Sulfide Nanoparticles," ACS Biomater. Sci. Eng, 2019, 5(3):1553-1560.
Marcus et al., "Current approaches and challenges in managing and monitoring treatment response in ovarian cancer," Journal of Cancer 5(1), 25 (2014).
Miranda et al., "Intrauterine photoacoustic and ultrasound imaging probe," Journal of Biomedical Optics 23(4), 046008 (2018).
Miranda et al., B. S. Photoacoustic micropipette. Appl. Phys. Lett. 2018, 113, 264103.
Ohnaga et al., "Capture of esophageal and breast cancer cells with polymeric microfluidic devices for ctc isolation," Molecular and clinical oncology 4(4), 599-602 (2016).

(56) References Cited

OTHER PUBLICATIONS

Pantel et al., "Circulating tumour cells in cancer patients: challenges and perspectives," Trends in molecular medicine 16(9), 398-406 (2010).

Parker et al., "Folate receptor expression in carcinomas and normal tissues determined by a quantitative radioligand binding assay," Analytical biochemistry 338(2), 284-293 (2005).

Parmar et al., "Paclitaxel plus platinum-based chemotherapy versus conventional platinum-based chemotherapy in women with relapsed ovarian cancer: the icon4/ago-ovar-2.2 trial.," Lancet (London, England) 361(9375), 2099-2106 (2003).

Poveda et al., "Circulating tumor cells predict progression free survival and overall survival in patients with relapsed/recurrent advanced ovarian cancer," Gynecologic oncology 122(3), 567-572 (2011).

Pradeep et al., "Hematogenous metastasis of ovarian cancer: rethinking mode of spread," Cancer cell 26(1), 77-91 (2014).

Siegel et al., "Cancer statistics, 2016," CA Cancer J Clin 66:7-30 (2016).

Siwowska et al., "Folate receptor-positive gynecological cancer cells: In vitro and in vivo characterization," Pharmaceuticals 10(3), 72 (2017).

Takao et al., "Enumeration, characterization, and collection of intact circulating tumor cells by cross contamination-free flow cytometry," Cytometry Part A 79(2), 107-117 (2011).

Wang et al., "In vivo photoacoustic molecular imaging of breast carcinoma with folate receptor-targeted indocyanine green nanoprobes," Nanoscale 6(23), 14270-14279 (2014).

Watanabe et al., "Multicolor detection of rare tumor cells in blood using a novel flow cytometry-based system," Cytometry Part A 85(3), 206-213 (2014).

Yang et al., "One-pot one-cluster synthesis of fluorescent and bio-compatible Ag14 nanoclusters for cancer cell imaging," Nanoscale (2015): 7(44):18464-18470.

Zhou et al., "Prognostic value of circulating tumor cells in ovarian cancer: a meta-analysis," PLOS One 10(6), e0130873 (2015).

Zhou et al., "Theranostic cus nanoparticles targeting folate receptors for pet image-guided photothermal therapy," Journal of Materials Chemistry B 3(46), 8939-8948 (2015).

U.S. Appl. No. 16/902,110, filed Jun. 15, 2020, by Smith et al.

* cited by examiner

Nanoparticle Formation Day 2

Nanoparticle Formation Day 5

FOLIC ACID FUNCTIONALIZED COPPER SULFIDE NANOPARTICLES FOR THE DETECTION OF OVARIAN CANCER CELLS IN FLOW

CROSS REFERENCE TO RELATED APPLICATIONS

This application claims priority to U.S. Provisional Application No. 62/808,442, filed Feb. 21, 2019, which is incorporated herein by reference in its entirety.

TECHNICAL FIELD

This disclosure relates to compositions and methods for detecting ovarian cancer cells by photoacoustic flow cytometry.

BACKGROUND

Ovarian cancer is the most fatal gynecological malignancy in the United States and is the fifth leading cause of cancer related death in women. Although advances in first-line ovarian cancer treatments have increased the rates of initial therapeutic success, the vast majority of patients (85-90%) will experience disease recurrence with a median survival time of only 12-24 months. Disease recurrence often manifests itself through ascite formation, elevated CA125 biomarker levels, and tumor development.

Unfortunately, these indicators are detected with variable success or after substantial disease progression, when treatment success is much lower. There has been growing interest in the presence of circulating tumor cells (CTC) as an indicator of patient prognosis. Ovarian CTCs are metastatic cells that detach from the primary tumor and disseminate into intraperitoneal fluid. Although ovarian tumor metastases preferentially grow in the intraperitoneal cavity, these tumor cells also circulate in the peripheral blood supply. In the majority of ovarian epithelial cancers, CTC presence has been shown to precede primary tumor growth, making CTC identification an attractive alternative to current methods of cancer detection. Furthermore, the presence of CTCs in patients with recurrent ovarian cancer has been associated with poorer patient outcomes. Thus, CTC detection has the potential to offer diagnostic information as well as inform future treatment for those with ovarian cancer.

Current clinical measures for CTC detection in blood lack the sensitivity for translation to clinical settings for ovarian cancer. Many of these methods, including the CellSearch system, rely on the presence of the EpCAM surface antigen in CTCs. EpCAM, however, is down-regulated in the process of epithelial-mesenchymal transition (EMT), which tumor cells undergo prior to detachment from the primary tumor. Furthermore, unlike other epithelial cancers, ovarian cancer's primary mode of metastasis is not hematogenous and ovarian CTCs enter the peripheral blood circulation in fewer numbers than those of breast, prostate, or lung cancer. Due to their rarity and the low sensitivity of EpCam, ovarian CTCs can evade detection by traditional enrichment methods. Therefore, there remains a need for methods and compositions to accurately and sensitively detect ovarian CTCs.

SUMMARY

The present disclosure is directed to a method of detecting an ovarian circulating tumor cell in a subject suspected of having cancer. The method comprises obtaining a test sample from the subject, contacting the test sample with a nanoparticle, wherein the nanoparticle is configured for uptake by an ovarian circulating tumor cell, optionally incubating the test sample with the nanoparticle for a period of time sufficient to allow an ovarian circulating tumor cell in the test sample to uptake the nanoparticle, removing from the test sample any free nanoparticle not taken up by an ovarian circulating tumor cell, illuminating the test sample with laser light, and detecting the presence of the ovarian circulating tumor cell in the subject when a photoacoustic signal generated by the nanoparticle is detected with an acoustic sensor.

The present disclosure is also directed to a method of detecting metastatic ovarian cancer in a subject. The method comprises obtaining a test sample from the subject, contacting the test sample with a nanoparticle, wherein the nanoparticle is configured for uptake by an ovarian circulating tumor cell, optionally incubating the test sample with the nanoparticle for a period of time sufficient to allow an ovarian circulating tumor cell in the test sample to uptake the nanoparticle, removing from the test sample any free nanoparticle not taken up by an ovarian circulating tumor cell, illuminating the test sample with laser light, and detecting the presence of metastatic ovarian cancer in the subject when a photoacoustic signal generated by the nanoparticle is detected with an acoustic sensor.

The present disclosure is also directed to a photoacoustic flow system comprising: a flow chamber configured to support a capillary tube, the flow chamber including a window and a slot; a pump system coupled to the capillary tube, the pump system including a first syringe pump filled with air and a second syringe pump containing a sample, wherein the first pump injects the air into the capillary tube, and the second pump injects the sample into the capillary tube to produce two-phase flow with alternating air and sample through the capillary tube; an optical fiber coupled to a laser and configured to transmit light to excite the sample in the capillary tube; an ultrasound transducer coupled to the window in the flow chamber, wherein the ultrasound transducer detects acoustic signals generated by excitation of the sample; an inverted fluorescence microscope including a stage for supporting the flow chamber and a camera aligned with the slot in the flow chamber for imaging the sample as it passes through the capillary tube; and a data acquisition system configured to receive the acoustic signals from the ultrasound transducer and the images from the camera to reconstruct and display a photoacoustic image of the sample.

Other aspects of the invention will become apparent by consideration of the detailed description and accompanying drawings.

BRIEF DESCRIPTION OF THE DRAWINGS

FIG. 2A shows a representative TEM image of FA-CuS NPs. Scale bar is 50 nm. FIG. 2B shows the size distribution of FA-CuS NPs. FIG. 2C shows a representative DLS intensity distribution of FA-CuS NPs. FIG. 2D is an absorbance curve of FA-CuS NPs.

FIG. 3B is the MALDI spectra from folic acid. FIG. 3C is the MALDI spectra of the FA-CuS NPs.

FIG. 5A shows a boxplot of log transformed peak integrals from cells alone, cells with NPs, and PBS. FIG. 5B shows a boxplot of log transformed peak integrals of Cell Alone, Cells with NPs, FA-CuS NPs, and PBS.

FIG. 13A shows a TEM image of folate capped copper sulfide nanoparticles. FIG. 13B shows photoacoustic signal generation at 1064 nm.

FIGS. 14A-14B show confocal images of SNPs (green) within the cell (FIG. 14A) negative control (FIG. 14B) SNPs 80 μg/mL. FIGS. 14C-14D show the PA effect generated from (FIG. 14C) negative control (FIG. 14D) 1 mg/mL SNPs.

DETAILED DESCRIPTION

Figure 1A:
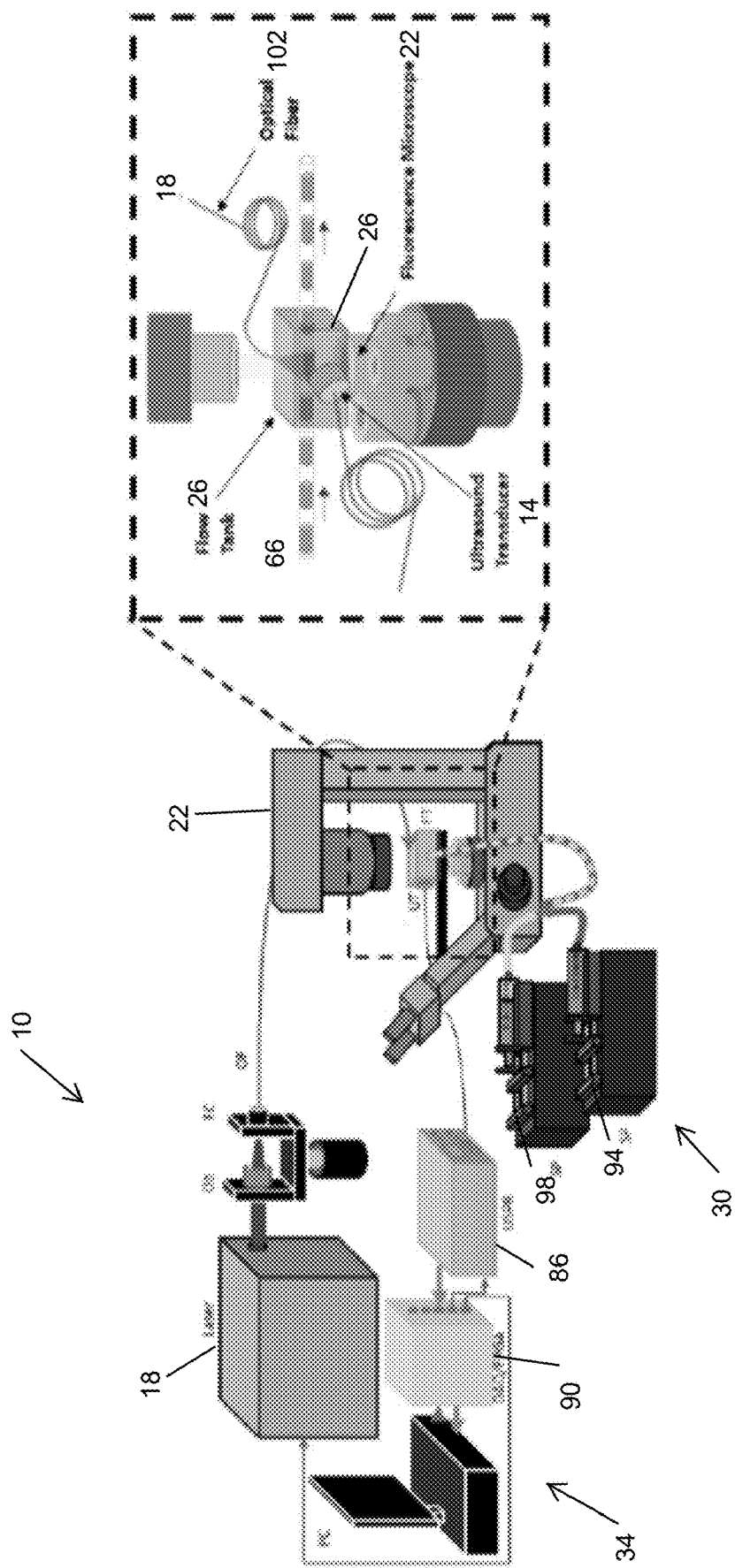
FIG. 1A illustrates a schematic illustrating a photoacoustic (PA) flow system according to an embodiment. Ob, objective lens; FC, fiber coupler; OF, optical fiber; FT, flow tank; UT, Ultrasound Transducer; USPR, ultrasound pulser receiver; DAQ/FPGA, data acquisition/field programmable gate array; SP, Syringe Pump.

The present disclosure relates to a system and a method for detection of ovarian circulating tumor cells (CTCs). The system includes a photoacoustic flow cytometer (PAFC) utilizing a customized flow chamber and a syringe pump. The method utilizes folic acid functionalized copper sulfate nanoparticles (FA-CuS NPs) for the PA detection of CTCs. The PAFC system was evaluated through the detection of NPs and tagged ovarian cancer cells within a two-phase flow system. For example, SKOV-3 were detected cells using FA-CuS NPs. showing the ability of the method disclosed herein to detect ovarian CTCs at physiologically relevant concentrations. By functionalizing the NPs with folic acid, the NPs were specifically designed to be taken up by ovarian cancer cells. Fluorescence microscopy indicated significant uptake of FA-CuS NPs by cells, such as SKOV-3 cells. This method produced high intensity PA signals for the non-invasive detection of ovarian CTCs, enabling the clinical application of CTCs to detect early stages of metastasis in ovarian cancer.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

PAFC has emerged as an effective method for the non-invasive detection of cancer cells, analysis of nanomaterials, and identification of bacteria. PAFC differs from traditional fluorescence flow cytometry by detecting analytes in flow by utilizing photoacoustics. The photoacoustic effect is generated when laser light is absorbed by a material that causes thermoelastic expansion, producing an acoustic wave that can be detected by an ultrasound transducer. Advantages of PAFC over traditional flow cytometry methods include simplicity, ease of translation to clinical settings, and the detection of CTCs at unprecedented depths in patient samples.

Recent studies have utilized PAFC systems for the detection of cells using endogenous and exogenous contrast. Near infrared (NIR) light-absorbing contrast agents such as indocyanine green dye, and metal NPs (e.g., gold and CuS) have been used for the selective labeling of cells and tissues in combination with photoacoustic imaging. Due to the improved penetration depth of NIR light within biological tissues, photoacoustic detection of absorbers can be performed at greater depths for clinical applications. Because of its great potential for use in the clinic, the combination of targeted NIR contrast agents with PAFC has generated considerable interest for the detection of CTCs.

PAFC in combination with targeted contrast agents provides an improved approach for high-throughput analysis of patient samples with enhanced accuracy and targeted detection of CTCs. One of the principal detection strategies for CTCs is the specific targeting of membrane proteins present on the cell of interest. One notable characteristic of ovarian CTCs is the overexpression of folate receptors located on their outer membrane. Folate receptor targeting is an ideal strategy for the identification of ovarian CTCs in blood because endogenous cells, which have higher expression of folic acid receptors, are generally luminal and have limited exposure to the bloodstream. Copper sulfide NPs (CuS NPs) have recently been recognized for their ability to target folate receptors expressed on cancerous cells. Combined with their biocompatibility, ease of synthesis, and absorption deep in the NIR, these NP contrast agents make an ideal targeting strategy for the detection of ovarian CTCs utilizing PAFC.

FIG. 1A illustrates a PAFC system 10 according to an embodiment. The system 10 includes a transducer 14 (e.g., ultrasound), a laser 18, a microscope 22 (e.g., fluorescence), a flow chamber 26, a pump system 30, and a data acquisition system 34. The flow chamber 26 is further illustrated in FIG. 1B and includes a base 38 and side walls 46, 50, 54, and 58 to form a receptacle. In one configuration, the receptacle is 2.5 cm×1.5 cm×7.5 cm and can comprise ABS thermoplastic or PLA plastic. The receptacle may include a fluid.

Figure 1B:
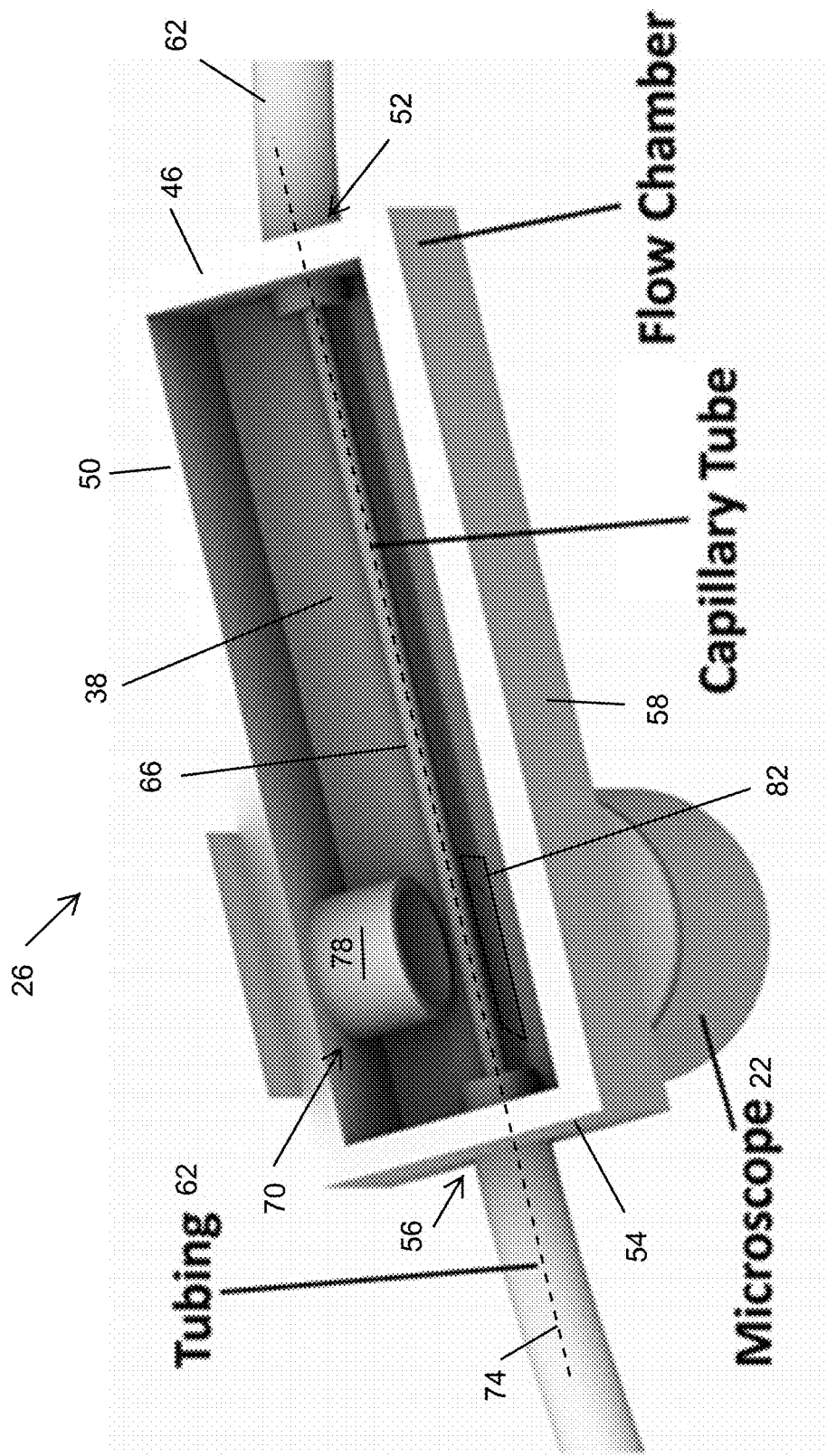
FIG. 1B illustrates a flow chamber for use in the photoacoustic flow system of FIG. 1A.

Side walls 46 and 54 include openings 52, 56 to receive tubing 62 and a capillary tube 66. The openings are approximately 5 mm in diameter to receive the tubing 62. The capillary tube 66 extends approximately the length of the receptacle or about the length of side walls 50 and 58. The capillary tube 66 is supported in position by the tubing 62 at each end of the capillary tube 66 as illustrated in FIG. 1B. One of the side walls 50, 58 includes an opening 70, which is oriented perpendicular to a longitudinal axis 74 defined by the capillary tube 66. The opening 70 is formed in side wall 50 or 58 at a height that is aligned with the height of the capillary tube 66. In one configuration, the opening 70 has a 1 cm diameter. The opening 70 is configured to receive the transducer 14. A cylindrical extension 78 surrounds the opening 70 on the inside of the receptacle, and is configured to receive a glass coverslip. Ultrasound gel may be applied to the glass for acoustic coupling between the glass and the transducer 14. In one configuration, the cylindrical extension 78 has a 1 cm diameter and a 6 mm length.

For real-time imaging, the flow chamber 26 includes a slot 82 formed within the base 38. In one configuration, the slot is 1 mm×3 mm and is positioned below the capillary tube 66. The slot is configured to receive a glass coverslip. The openings 52, 56, 70 may be sealed with silicone to prevent leakage.

With reference to FIG. 1A, the transducer 14 is electrically coupled to an ultrasound pulser/receiver 86 (5077PR Square Wave pulser/receiver, available from Olympus Inc.) where the detected signal can be received and amplified (e.g., with a 59 dB gain). The output of the ultrasound pulser/receiver 86 is transmitted through a filter to an oscilloscope equipped with a built-in field programmable gate array 90 (e.g., NI PXIe-5170R, available from National Instruments Corporation).

The pump system 30 includes a first syringe pump 94 and a second syringe pump 98. The pump system 30 is coupled to an inlet of the tubing 62 via a T-junction connector. In one embodiment, the first syringe pump 94 is filled with air, and the second syringe pump 98 is filled with a sample to be analyzed. The resulting two-phase flow with alternating air and sample through the capillary tube will produce sample volumes for testing in the flow chamber 26. The sample may need to be lightly vortexed immediately before being tested to maintain a consistent distribution of cells. In addition, the syringe may be rotated every few minutes in order to prevent the cells from settling in the solution. The outlet tubing 62 is coupled to a container with 10% bleach, to dispose of cells after they exit the flow chamber 26.

The configuration of the flow chamber 26 allows for consistent and repeatable alignment between the transducer 14 and light from the laser 18 with minimal calibration. When placed correctly within the flow chamber 26, the quartz capillary tube 66 ensures that the transducer 14 and laser 18 are directly aligned.

The flow chamber 26 is positioned on the stage of the microscope 22 in the field of view (e.g., the field of view is aligned with the slot 82). The laser 18 includes an optical fiber 102 positioned above the flow chamber 26 to illuminate the capillary tube 66 inside the receptacle. The entire length of the capillary tube 66 may be illuminate or only a portion thereof. The optical fiber 102 channels a diode-pumped solid state laser operating at a wavelength of 1,053 nm (QUANTAS-Q1D-1053, available from RPMC Lasers Inc.) and directs the laser light to the sample in the capillary tube 66. The laser light incident on the sample and the transducer used to measure the photoacoustic effect are both unfocused.

The energy of the laser 18 incident on the test sample is approximately 8 mJ and the 10 Hz laser rate is sufficient to illuminate each test sample multiple times as it passes through the flow chamber 26. The flow of the test samples through the flow chamber 26 and the firing of the laser 18 is recorded using a microscope-mounted digital camera (e.g., available from Thorlabs, Austin Tex.). These recordings are utilized to correlate the photoacoustic signal recorded by the transducer 14 with the firing of the laser 18. As the test samples pass in front of the firing of the laser 18, the signal can then be correlated to the resulting photoacoustic signal for analysis. At a sampling rate of 10 Hz, the laser 18 illuminates each test sample several times.

The ultrasound transducer detects photoacoustic signals generated by illumination of the test sample with the laser 18 and transmits the signal data to the pulser/receiver, the oscilloscope, and to the data acquisition system for processing. The data is processed and transferred to a computer, where the reconstructed image is displayed in real time. Multipurpose programmable function input/output lines, built into the FPGA, are used for custom triggering and synchronization of the imaging system.

Figure 6:
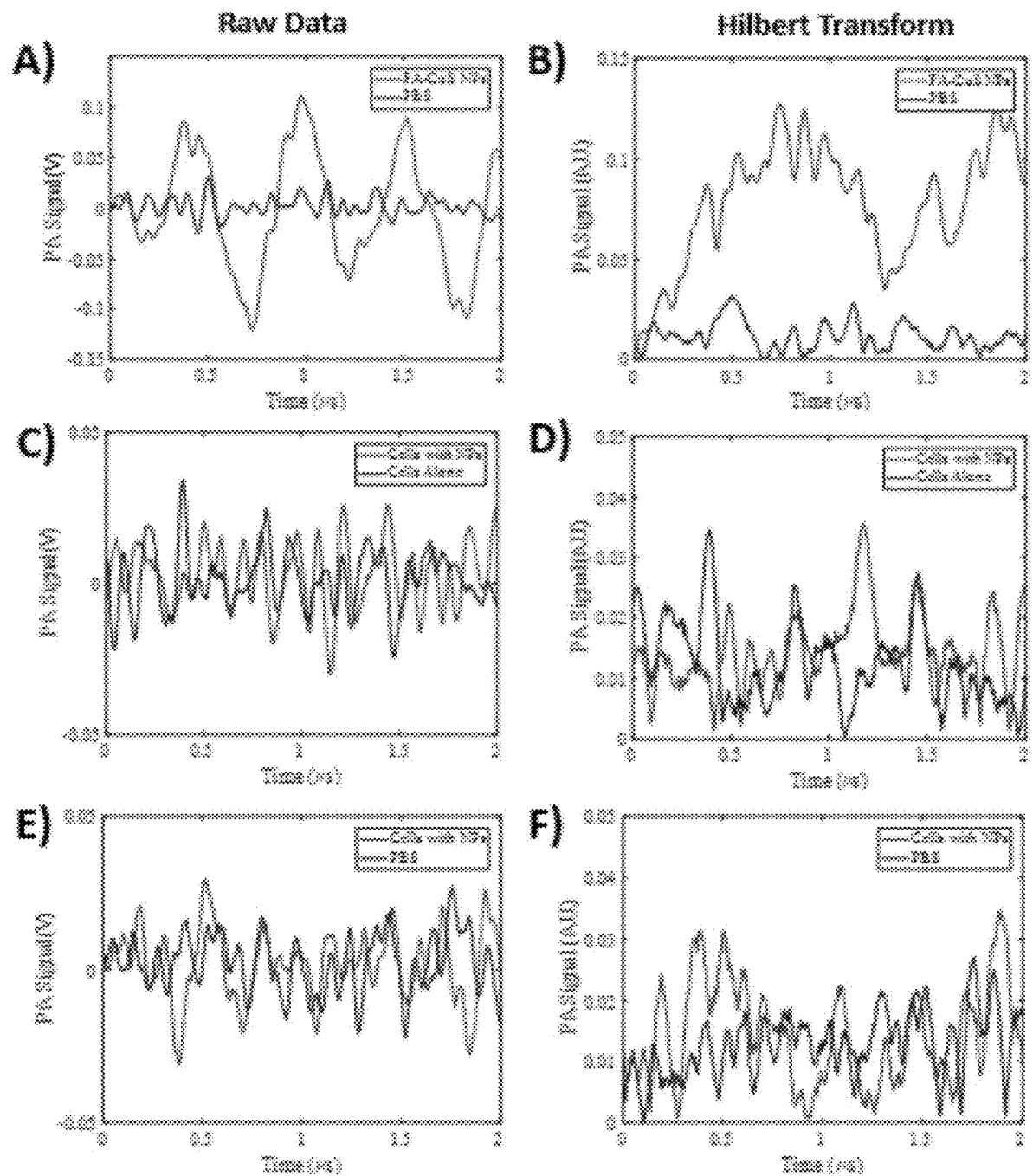
FIG. 6 shows the data analysis of the PA signals. Representative raw data signals from FA-CuS NPs and PBS (graph A) and the Hilbert transform of the data (graph B). Representative raw data signal from Cells with NPs and Cells alone (graph C) and corresponding Hilbert transform (graph D). Representative raw data signal from cells with NPs and PBS (graph E) and corresponding Hilbert transform (graph F).

For each signal acquisition, s(t), the Hilbert transform, H[s(t)], is calculated in order to create an analytic signal. A complex envelope, se(t), is generated by calculating the magnitude of the analytic signal, such that $s_e(t)=\sqrt{(s^2(t)+H^2[s(t)])}$ and integrate the envelope to measure the total signal resulting from each acquisition. The signals from each test group (i.e., PBS, tagged cells, FA-CuS NPs, cells alone) are compared utilizing a t-test in R statistical software. Raw photoacoustic signals and their Hilbert transforms are presented in FIG. 6.

Figure 7A:
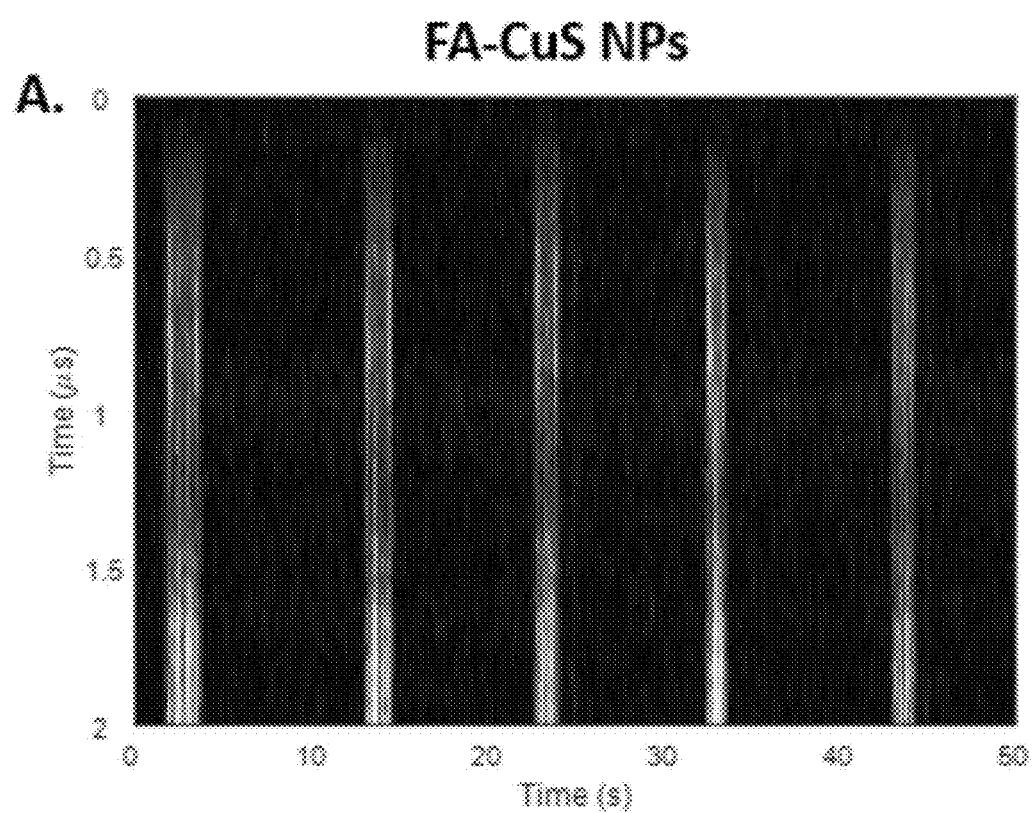
FIGS. 7A-7B show photoacoustic image reconstructions of 100 μg/mL folic acid capped copper sulfide nanoparticles (FA-CuS NPs) in 2% TWEEN and PBS (FIG. 7A) and PBS with 2% TWEEN in the photoacoustic flow system (FIG. 7B). The alternating FA-CuS sample generates a very strong photoacoustic signal.
Figure 7B:
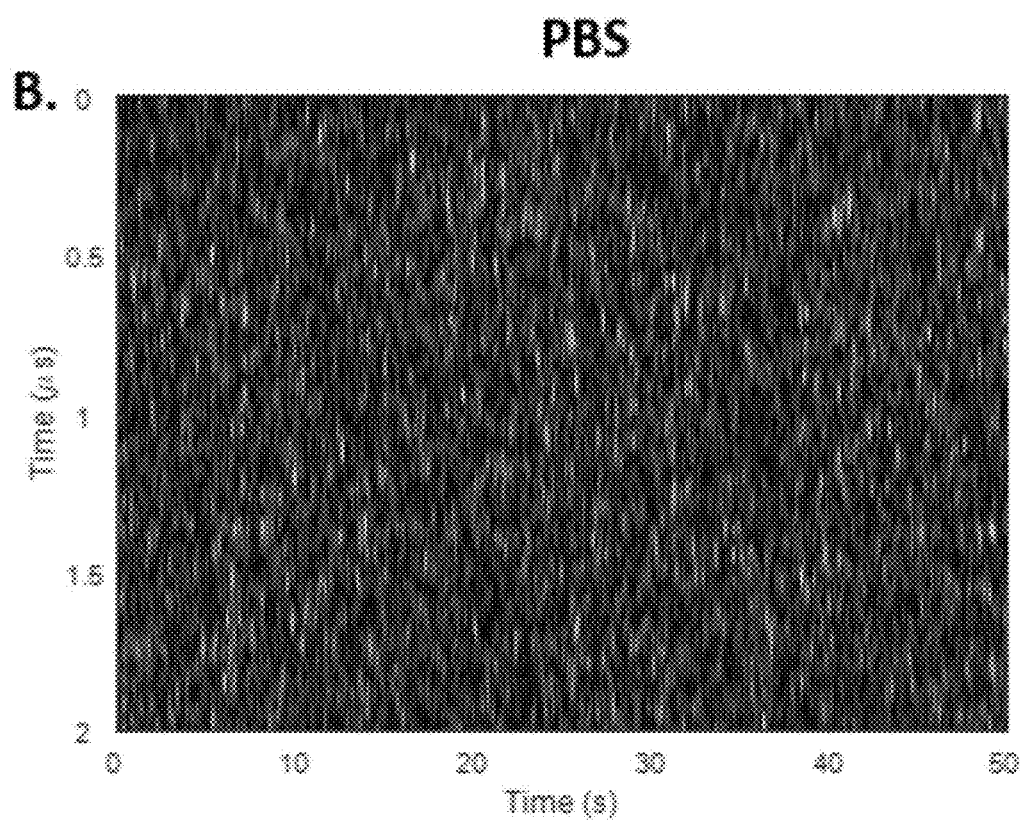

For image reconstruction, the complex envelope is normalized based on the maximum peak across the whole run. If comparing a series of runs, the complex envelope is normalized using the maximum peak across the entire series. Following normalization, each acquisition is converted into a series of pixel values. Each series of pixel values are represented as a column in the image reconstruction. Representative reconstructions of PBS and the FA-CuS NPs signals are shown in FIGS. 7A and 7B, where both images were normalized using the maximum peak across both runs.

The test sample is taken from a subject for the purpose of detecting the presence or absence of ovarian tumor cells. The test sample can be any fluid sample suitable for use according to the methods of the invention. Non-limiting examples include intraperitoneal fluid, ascites or blood; and peripheral body fluids including blood, cerebrospinal fluid, saliva, vaginal fluid, mucus, and/or urine.

According to the methods of the invention, the test samples are contacted with a nanoparticle, wherein the nanoparticle is configured for uptake by an ovarian circulating tumor cell. Contacting of the test sample with the nanoparticle(s) may occur according to any method suitable for use, including both, static, or dynamic incubation and under any conditions which facilitate the uptake of the nanoparticle(s) and optional marker(s) by the ovarian tumor cells. The optional incubation step can occur over any duration from 1 to 5 hours. In one non-limiting embodiment, the test sample is incubated with the nanoparticle(s) and optional marker(s) for 2 hours.

As used herein, the term "nanoparticle" is defined as a particle having at least one dimension on the order of nanometers (e.g., 1-1,000 nm). In various embodiments, the nanoparticles have a mean diameter of from about 3 nm to about 20 nm, from about 5 nm to about 15 nm, or 9 nm. In other embodiments, the nanoparticles have a hydrodynamic diameter of about 25 nm to about 150 nm, from about 50 nm to about 125 nm, or 74 nm. The nanoparticles can be any nanoparticle suitable for use according to the methods of the invention. Non-limiting examples include carbon-based nanoparticles, ceramic nanoparticles, metal nanoparticles, polymeric nanoparticles, magnetic nanoparticles, and/or lipid-based nanoparticles.

In various embodiments of the invention, the nanoparticles comprise a metal, including, but not limited to, copper sulfide, silver nitrate, and/or gold. The nanoparticles can also be modified to include functional modifications and/or labels. Examples of functional modifications include, but are not limited to folic acid, glutathione, antibodies, small molecules and aptamers.

Examples of labels include, but are not limited to, chromophores, chemiluminescent moieties, bioluminescent moieties, fluorescent moieties and metals. Exemplary chromophores include, but are not limited to, 3,3'-diaminobenzidine (DAB); 3-amino-9-ethyl carbazole (AEC); Fast Red; FD&C Yellow 5 (Tartrazine); Malachite Green Carbinol hydrochloride; Crocein Scarlet 7B (Dark Red); Erloglaucine (Dark Blue); Crystal Violet (Dark Purple); Bromophenol Blue; Cobalt(II) Chloride Hexahydrate (Red); Basic Violet 3; Acid Blue 9; Acid Red 71; FD&C Blue 1 (Brilliant Blue FCF); FD&C Red 3 (Erythrozine); and FD&C Red 40 (Allura Red AC). Suitable fluorescent labels that may be used are known in the art, and include but are not limited to fluoresceins, rhodamines, coumarins, pyrenes, cyanines, squaraines, and boron-dipyrromethenes. Fluorescent label reagents will typically include the fluorescent label along with one or more reactive moieties, such as N-succinimidyl esters or isothiocyanates. For example, fluorescent label reagents that are commercially available include but are not limited to: Texas Red™ (sulforhodamine 101 acid chloride), 5- and 6-carboxyfluoresceins and esters thereof; fluorescein isothiocyanate; BODIPY® dyes commercially available from Molecular Probes; Alexa Fluor® dyes commercially available from Molecular Probes; CyDye fluors commercially available from GE Healthcare Biosciences; HiLyte™ Fluor Dyes available from AnaSpec; and VivoTag™ fluorophores available from PerkinElmer. The fluorescent reagent can be chosen based on desired excitation and emission spectra. Also exemplary of fluorescent reagents are macromolecules that emit an optically detectable signal, including fluorescent proteins, such as a green fluorescent protein (GFP) or a red fluorescent protein (RFP). A variety of DNA sequences encoding proteins that can emit a detectable signal or that can catalyze a detectable reaction, such as luminescent or fluorescent proteins, are known and can be used in the methods provided herein. Exemplary genes encoding light-emitting proteins include, for example, genes from bacterial luciferase, firefly luciferase, aequorin, *Renilla* luciferase, and green fluorescent protein. In one, non-limiting embodiment the nanoparticle comprises copper sulfate, functionalized with folic acid, and labeled with the fluorescent label Texas Red™.

According to the methods of the invention, the nanoparticle(s) are configured for uptake by circulating ovarian tumor cells.

The methods of the invention can further comprising incubating the test sample with an optional marker, wherein the marker is configured to identify a particular cell population or a subset thereof in the test sample. In one non-limiting example the marker is configured for uptake by a cancer cell. Non-limiting examples of an optional marker include a second nanoparticle (antibodies, antigens, small molecules, aptamers and genetically encoded proteins). The marker can further comprise a label or tag as defined above. In one, non-limiting embodiment the marker comprises a second nanoparticle comprising silver nitrate and functionalized with glutathione.

Once the contacting and optional incubation steps are completed, any free nanoparticle(s) and/or optional marker(s) that has not been taken up, is removed from the test sample. Removal of free nanoparticle(s) and/or marker(s) can be accomplished though any suitable method including, but not limited to, washing of the test sample, magnetic removal, size filtration or centrifuging of the test sample.

Once the free nanoparticle(s) and marker(s) have been removed, the test sample can be assessed for the presence or absence of nanoparticle and optional markers taken up by circulating ovarian tumor cells. The assessment can occur via any method suitable for assessing the cells in the test samples. This includes, imaging, illumination, photoacoustic or magnetic detection. One method of illumination uses various wavelengths of laser light. In various embodiments the laser light has a wavelength of between about 250 and 1400 nm, between about 350 nm and about 650 nm, between about 350 nm and about 500 nm, about 430 nm, between about 700 to about 1400 nm, between about 950 and 1150 nm, and about 1050 nm. The test samples can be illuminated with different wavelengths in order to assess the nanoparticle(s) and the optional marker(s) separately or at the same time.

The method of the invention can also include the optional step of circulating the test sample through a capillary tube in a test chamber filled with water. This method can also include alternating air and the test sample through the capillary tube.

Circulation can be accomplished via any method suitable for use with the present invention. The capillary tube can be any diameter suitable for use in the present invention.

The final step, according to the methods of the invention, is to use an acoustic sensor to detect a photoacoustic signal generated by the presence of nanoparticle(s) in circulating ovarian tumor cells in the test samples from a subject if the test sample contains circulating ovarian tumor cells. This allows the acoustic detection of circulating ovarian tumor cells using a photoacoustic signal. Examples of acoustic sensors include transducers or piezo electric crystals with detection mechanisms ranging from 10 to 100 MHz. Other sensors include optical sensors i.e., fabry perot.

The methods of the invention can also be used to detect the presence of metastatic ovarian cancer since, by definition, metastatic ovarian cancer comprises the presence of circulating ovarian tumor cells. Thus, detection of circulating ovarian tumor cells in the test sample indicates the presence of metastatic ovarian cancer in the subject.

EXAMPLES

Example 1—Materials and Methods

Folic acid, and sodium sulfide nonahydrate ($Na_2S_9H_2O$) were purchased from Sigma Aldrich (St. Louis, Mo., USA). Copper (II) chloride ($CuCl_2$) was purchased from Acros Organics (Geel, Belgium). Amicon Ultra-4 and Ultra-15 (30 kDa MWCO) centrifugal columns were purchased from EMD Millipore (Burlington, Mass., USA). Texas Red™-X succinimidyl ester fluorescent dye was purchased from ThermoFisher (Waltham, Mass., USA) DAPI (4,6-diamidino-2-phenylindole) was purchased from Molecular Probes (Waltham, Mass., USA). Folic Acid free RPMI 1640 media, McCoy's 5A cell culture media, and the antibiotics penicillin and streptomycin were purchased from Gibco (Grand Island, N.Y., USA). Fetal bovine serum (FBS) was purchased from Sigma Aldrich (St. Louis, Mo., USA) and trypsin 0.25%, 2.21 mM EDTA 1× was purchased from Corning (Corning, N.Y., USA).

Synthesis and Fluorescent Tagging of FA-CuS NPs. FA-CuS NPs were synthesized as previously described (M. Zhou, S. Song, J. Zhao, et al., "Theranostic CuS nanoparticles targeting folate receptors for PET image-guided photothermal therapy," *Journal of Materials Chemistry* B 3(46), 8939-8948 (2015)), but with minor modifications. Briefly, 100 µL of 1 M $Na_2S$ were added to 100 mL of a 1 mM $CuCl_2$ solution containing 0.16 mg of folic acid at room temperature under constant stirring for five minutes. At which point the reaction was heated to 90° C. in an oil bath. Once the oil bath reached 85° C. the reaction was heated for 1 hour, gradually turning to a dark green color and then removed from the heat. The FA-CuS NP solution was transferred to an ice bath, allowed to reach temperature, and stored at 4° C. Prior to concentrating and purifying the synthesized NPs, the reaction mixture was raised to a pH of ~10. The particles were concentrated using a 30 kDa MWCO centrifugal filter and were washed 4 times with DI water (pH ~10.) The particles were then resuspended in PBS and stored at 4° C. until use.

To fluorescently label the FA-CuS NPs, Texas-Red™-X succinimidyl ester (0.2 mg dissolved in DMSO), was added to a solution containing 2 mg of FA-CuS NPs in 0.1 M sodium bicarbonate (pH ~9) buffer. The reaction was stirred for 1 hour and purified by a centrifugation column by spinning at 4000×g for 10 minutes (30 kDa MWCO). It was then washed 3 times with 0.1 M sodium bicarbonate buffer (pH ~9) and subsequently with DI water until a negligible concentration of fluorescence was observed in the flow-through.

Characterization of FA-CuS NPs. Absorption of FA-CuS NPs and fluorescence of the Texas Red™-X modified NPs was determined using an ultraviolet-visible (UV-VIS) and fluorescence spectrophotometer (Molecular Devices, San Jose, Calif.). The FA-CuS NPs size was measured by transmission electron microscopy (TEM, CM12, Phillips, Tokyo, Japan) at an accelerating voltage of 80 kV. Size distribution of the NPs was determined using dynamic light scattering (DLS, Zetasizer Nano Malvern, Malvern, UK). Successful conjugation of the particles to folic acid was determined by time-of-flight/time-of-flight matrix assisted laser desorption/ionization (MALDI-TOF/TOF, AB SCI EX 4800, Foster City, Calif.). The laser power was set to 2825 $W/cm_2$ at 2500 shots/spectrum. Spots were prepared using a 1:1 ratio of sample to -Cyano-4-hydroxycinnamic acid (CHCA) matrix (EMD Millipore). The instrument was run in the positive ion mode at a mass range of 200-1200 Da with a focus mass of 440 Da.

Cell Culture. The cell line SKOV-3 (human ovarian cancer cell) was obtained from ATCC (American Type Culture Collection, Manassas, Va., USA). SKOV-3 cells were cultured in McCoy's 5A medium supplemented with 10% FBS, 100 U/mL penicillin, 100 µg/mL streptomycin, and maintained at 37° C. in a humidified 5% $CO_2$ incubator. For all experiments cells were incubated in folic acid-free RPMI-1640 media supplemented with 10% FBS, 100 U/mL penicillin, and 100 µg/mL streptomycin. All cells used were at or below passage 7 in this study.

Tagging CTC's for In Vitro Flow Detection. Experiments with tagged cells were performed on SKOV-3 cells that had been incubated in folic acid-free RPM I-1640 media for at least 24 hours. Cells were seeded at a density of 0.05×10⁶ cells/mL in a 24 well plate. The following day, cells were incubated with 400 µg/mL of FA-CuS NPs in folic acid-free RPMI-1640 media for 2 hours. Following this incubation, the cells were trypsinized with 0.25% trypsin with EDTA. Folic acid-free RPMI-1640 media was added and the cells were centrifuged at 123×g for 6 minutes. Following removal of the supernatant, the cell pellet was resuspended in PBS and centrifuged twice to remove any unbound NPs. Finally, the cells were resuspended in PBS with 2% TWEEN solution and diluted to 1000 cells/mL for subsequent experiments. All cell counts were performed using trypan blue and a hematocytometer.

In Vitro Cellular uptake of FA-CuS NPs. Prior to incubation with fluorescent FA-CuS NPs, cells were seeded on glass coverslips in a 24 well plate at a density of $0.05 \times 10^6$ cells per well in folic acid-free RPMI-1640 media. After 24 hours, and at approximately 25% cell confluency, the cells were incubated with fluorescently tagged NP concentrations of 100 µg/mL, 200 µg/mL, and 400 µg/mL in folic acid free RPMI-media. After incubation at 37° C. for 2 hours, all wells were gently rinsed with PBS, fixed with 3.7% formaldehyde, permeabilized with 0.1% Triton-X, and stained with DAPI for cell nuclei identification. The coverslips were then rinsed with PBS and mounted on glass slides using ProMount Diamond Antifade (ThermoFisher, Waltham, Mass.). Fluorescence microscopy was performed using a Leica DMI6000B microscope (Leica Microsystems Inc., Buffalo Grove, Ill.).

Flow System Architecture. A schematic of the experimental setup is provided in FIG. 1A. Dual syringe pumps (DUAL-1000 US, New Era Pump) injected both the sample and air simultaneously via 3.1 mm Masterflex platinum cured silicone tubing into a 1.5 mm capillary tube inside of a custom 3D printed flow tank. The sample and air were pumped at rates of 20 and 40 µL/minute respectively. The dual pumping of the syringe pumps produced two phase flow with alternating air and sample which flowed through a capillary tube that was surrounded by water within the flow tank. As the sample passed through the capillary tube it was irradiated by an optical fiber channeling a diode-pumped solid-state laser (QUANTAS-Q1D-1053, RPMC Lasers Inc.) operating at a wavelength of 1053 nm. The laser provided an excitation light with a full width half maximum (FWHM) of 8-ns at a pulse repetition rate of 10 Hz. A 10× objective with a 0.25 numerical aperture (NA) (LMH-10X-532, Thorlabs) was used to couple light to a 550 µm diameter multi-mode optical fiber. The optical fiber was held stationary such that a section of a capillary tube (QF150-75-10, Sutter) was illuminated by the laser with a pulse-energy of approximately 8 mJ. PA signals were detected using an unfocused 50 MHz transducer with an element diameter of 6 mm and a −6 dB fractional bandwidth of 82% (V214-BB-RM, Olympus). The ultrasound transducer was positioned on a glass window inserted into the side of the flow cell, perpendicular to the flow. Acoustic coupling between the glass window and a 50 MHz transducer was achieved using ultrasound gel. Signals detected by the transducer were sent to an ultrasound pulser/receiver (5077PR Square Wave pulser/receiver, Olympus Inc.). Amplification was performed through a 59-dB gain. A multipurpose reconfigurable oscilloscope (NI PXIe-5170R, National Instruments Corporation), equipped with a built-in field programmable gate array (FPGA), was used for data acquisition. Data was processed and transferred to a computer, where the reconstructed image was displayed in real time. Multipurpose programmable function input/output lines, built into the FPGA, were used for custom triggering and synchronization of the imaging system. The flow tank was mounted on the stage of an inverted fluorescence microscope (VWR, Bridgeport, N.J.), and a viewing port in the base of the cell allowed for the monitoring of cells and contrast agent in flow. The microscope image was recorded using a digital camera (Thorlabs, Austin Tex.), and used to track the position of the samples as they passed through the flow system.

PA Detection of Labeled CTCs. Samples containing dilutions of tagged and untagged SKOV-3 cells were pumped through the system along with 2% TWEEN in PBS as a negative control, and FA-CuS NPs as a positive control. The samples traveling through the capillary tube and across the path of the laser were monitored by a camera and were correlated to the resulting PA signal recorded by the ultrasound transducer. Measurements were taken for samples containing 1000 cells/mL in 2% TWEEN in PBS that had been incubated with FA-CuS NPs, and the same concentrations of cells alone in 2% TWEEN in PBS.

Statistical Analysis. Differences in PA signal generation between PBS, 1000 cells/mL, and NP tagged 1000 cells/mL were compared using Welch t-test after a log transformation of the data. Differences between conditions were considered statistically significant at $p<0.05$. Statistical tests were run using R statistical software.

Silver Glutathione Nanoparticles. SNPs were synthesized using glutathione and silver nitrate. The reaction took place over 7 days, while stirring at 60° C. Particle synthesis was monitored by UV-Vis spectroscopy and further characterized by transmission electron microscopy (TEM). Resulting SNPs were introduced to cancer cells at varying concentrations in culture, and imaged using light field, and confocal microscopy. The photoacoustic response of SNPs at a concentration of 1 mg/mL was measured using a miniature ultrasound transducer (Imasonic) while the particles were stimulated at a wavelength of 432 nm with a Nd/Yag sapphire laser (Symphotic Tii Corporation, Tatanya LS21340-LT40 laser system).

Example 2—Synthesis and Characterization of FA-CuS NPs

Figure 2A:
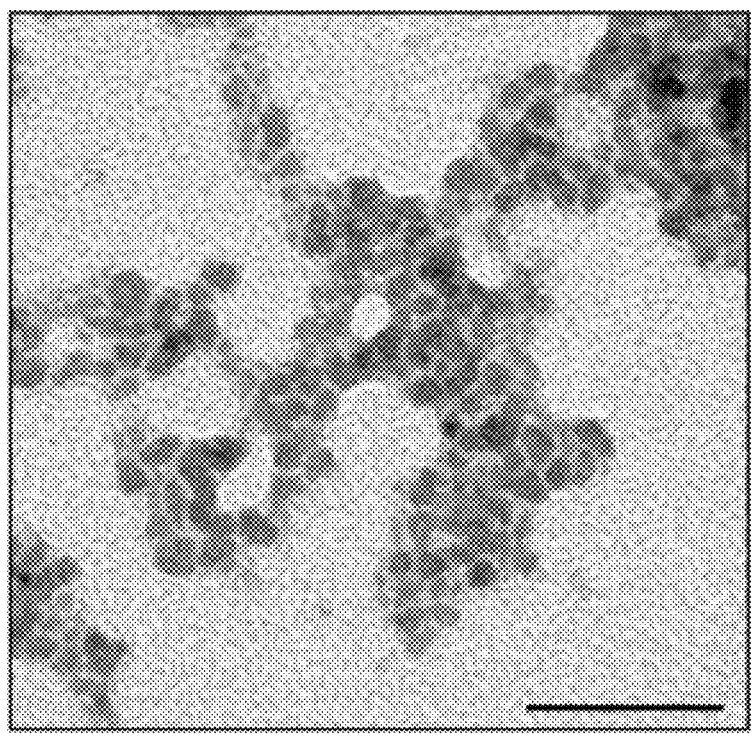
FIGS. 2A-2D show the characterization of folic acid functionalized copper sulfide nanoparticles (FA-CuS NPs).
Figure 2B:
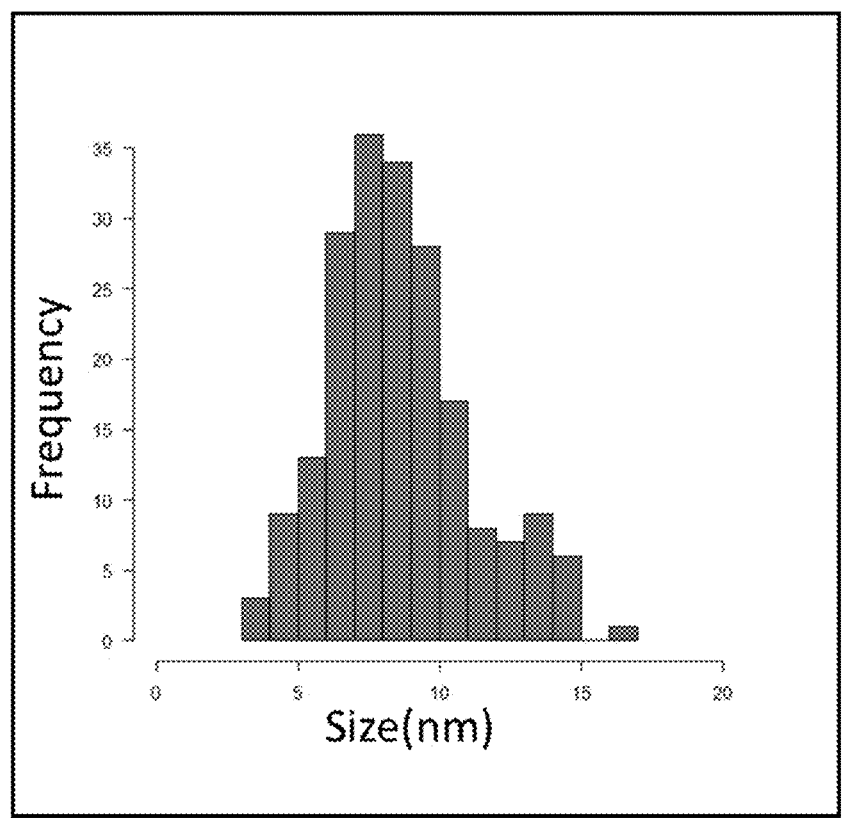
Figure 2C:
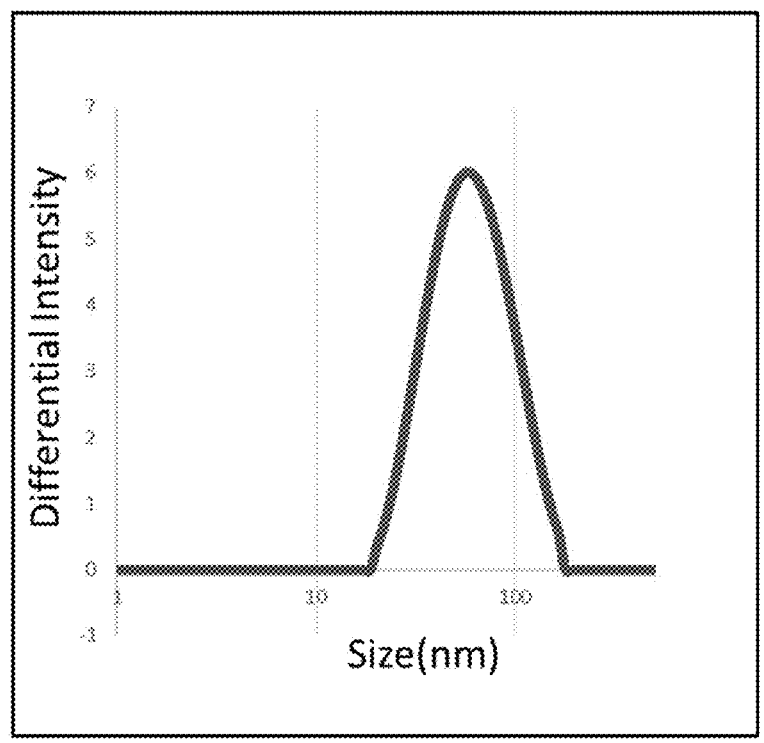
Figure 2D:
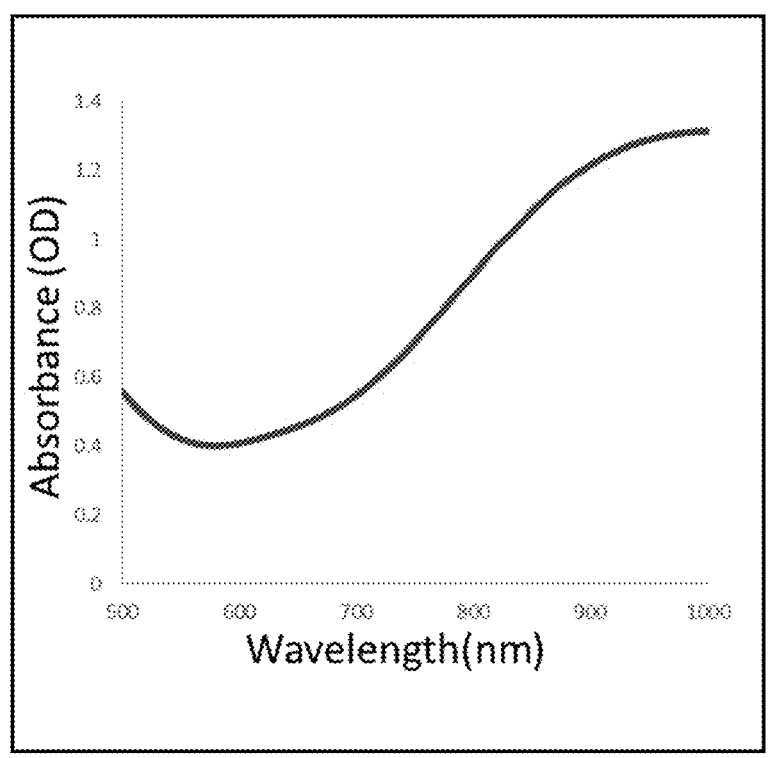

CuS NPs with their ease of synthesis, low cytotoxicity, biodegradability, and absorption in the NIR are ideal for PA applications. FA-CuS NPs were synthesized, and utilized as contrast agents for the specific detection of ovarian CTCs within a custom flow system. The FA-CuS NPs have characteristic NIR absorption from CuS as shown in FIG. 2D.

This absorbance in the NIR allows the NPs to be irradiated deep in tissues, making them an ideal candidate for in vivo applications. In order to further characterize the NPs, TEM, DLS, and MALDI-TOF-MS were used. FIG. 2A shows a TEM image of the FA-CuS NPs which is representative of the size and distribution of the NPs. TEM measurements were performed manually utilizing ImageJ. To more accurately measure size, the images were thresholded, and a watershed function was applied to separate the particles for measurement. The size of individual NPs (n=200) was quantified by taking measurements of the vertical and horizontal diameters perpendicular to one another. The two diameters were averaged for each of the NPs to more accurately represent the individual FA-CuS NP diameter. The measured size distribution can be seen in FIG. 2B, where the average measured mean diameter from TEM was approximately 8.6 nm. The particles were analyzed by DLS which showing an average cumulative hydrodynamic diameter of 73.6 nm and a representative measurement FIG. 2C. The difference between the DLS measurements and the calculated diameter from the TEM images were likely caused by both the folic acid shell and aggregation in the sample.

Figure 3A:
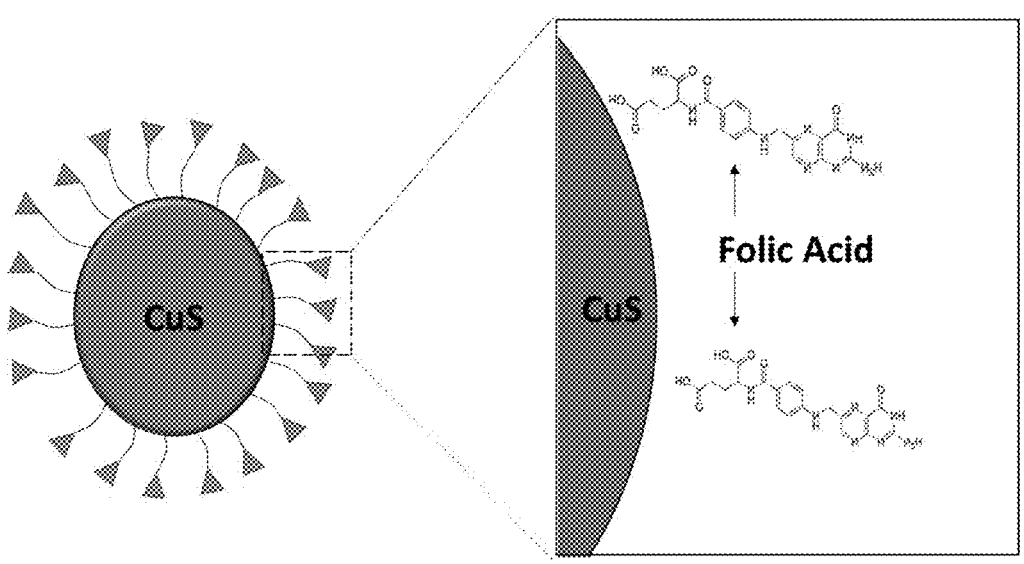
FIGS. 3A-3C show the FA-CuS NP capping strategy (FIG. 3A).
Figure 3B:
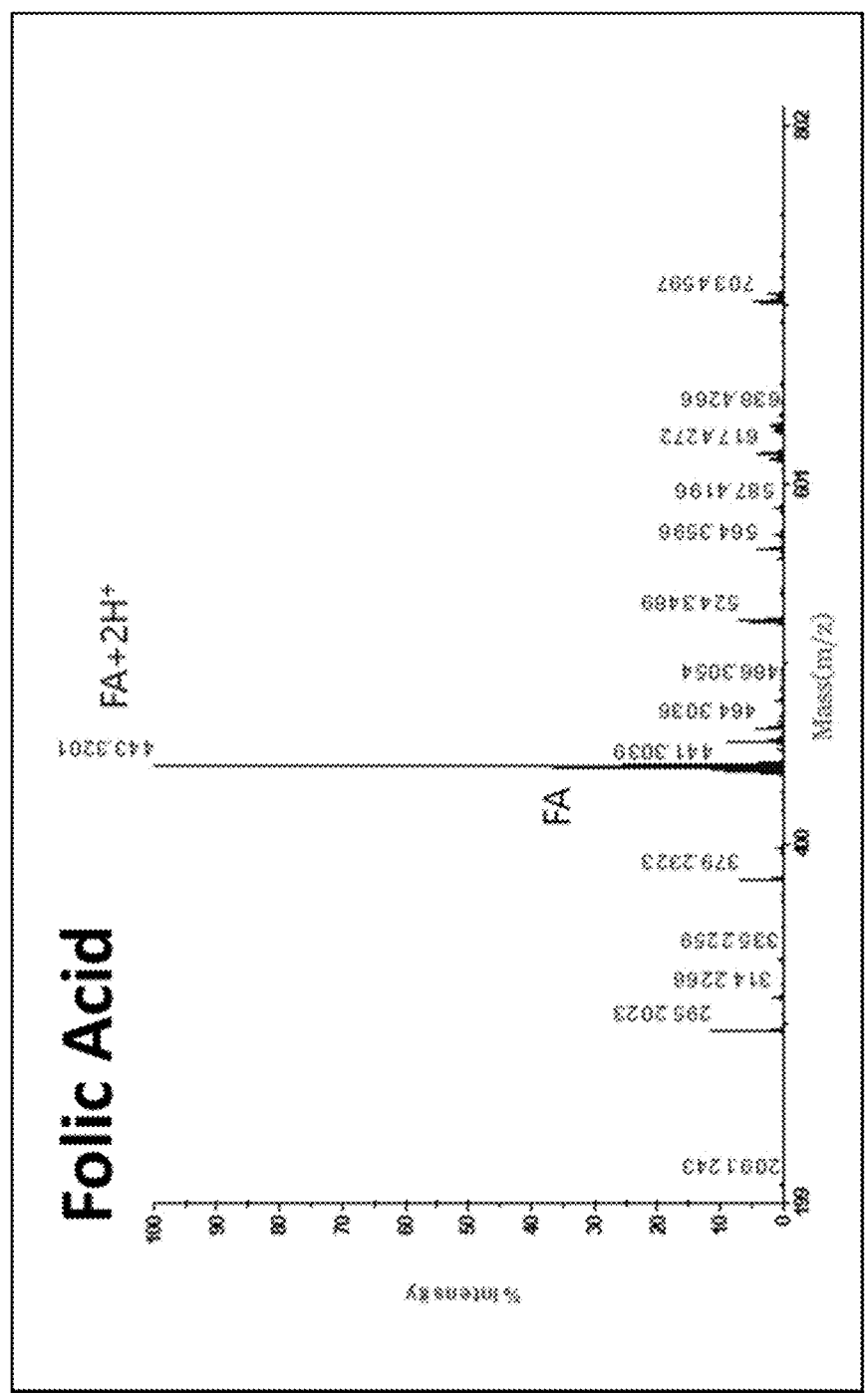
Figure 3C:
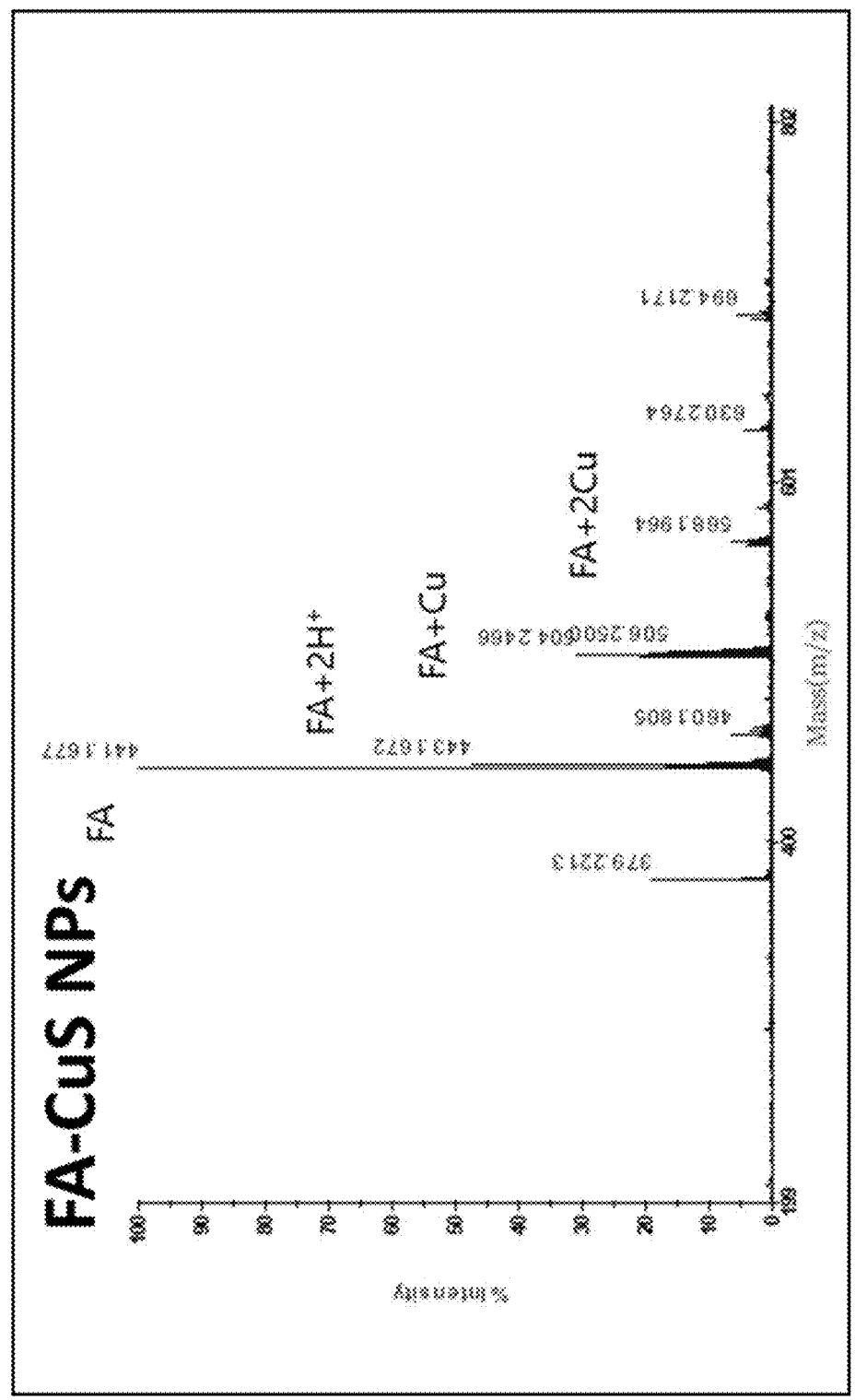

The functionalization of folic acid to the CuS NPs was critical for use in tagging ovarian cancer cells. The particles were analyzed to determine successful folic acid functionalization through MALDI-TOF. A saturated solution of folic acid in water was used to generate the positive control mass spectra shown in FIG. 3B. Protonation of the folic acid (441.40 Da) resulted in a 2 Da increase corresponding to the most abundant peak recorded, 443.32 Da. FA-CuS NPs were subsequently analyzed to produce the spectra shown in FIG. 3C. Folic acid was successfully identified in the NPs, producing two peaks at 441.17 and 443.17 Da. Mass shifts corresponding to the addition of copper atoms were identified in the spectra. Masses 504.25 and 506.25 corresponded to folic acid (441.17 or 443.17 Da). The addition of a single copper atom (63.55 Da) and mass 588.17 was assumed to be folic acid plus the addition of two copper atoms. Results from the MALDI-TOF analysis of FA-CuS NPs suggested that the folic acid was bound to the CuS NPs.

Example 3—In Vitro Uptake of FA-CuS NPs

Figure 4:
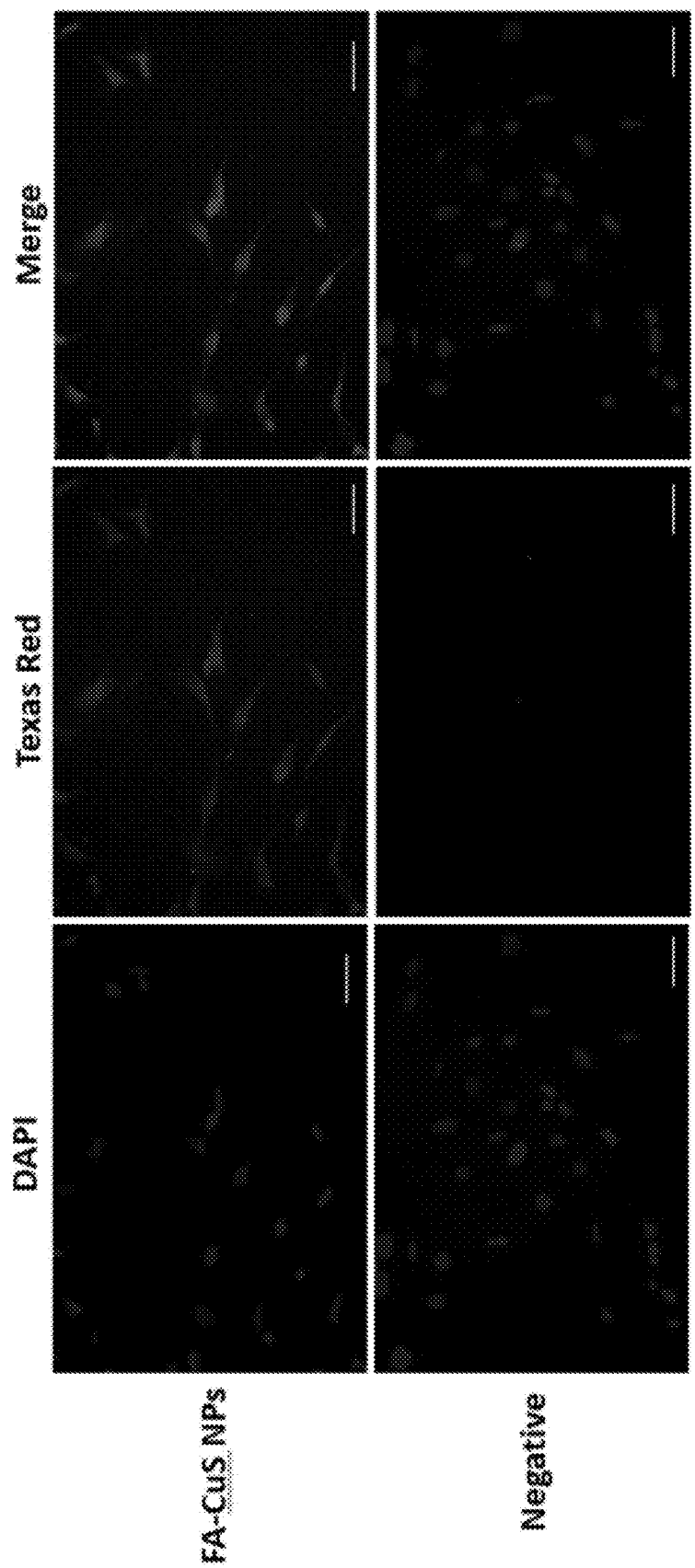
FIG. 4 shows representative fluorescence images of SKOV-3 cells incubated with and without 400 μg/mL fluorescently tagged FA-CuS NPs for 2 hours. Scale bar is 50 μm. Cell nuclei were stained with DAPI.

To investigate the cellular uptake of our FA-CuS NPs, fluorescently tagged NPs were incubated with SKOV-3 cells and then imaged using fluorescence microscopy. The folate receptor, which is often over-expressed on the surface of ovarian cancer cells, has remained an ideal target for NPs and other PA contrast agents. In this study, SKOV-3 cells were selected due to the high expression of the folate receptor on their outer membrane. FA-CuS uptake was measured by fluorescence as compared to the negative control. SKOV-3 cells incubated with the fluorescently tagged NPs displayed fluorescent intensity throughout the cell following the uptake of the FA-CuS NPs, as seen in FIG. 4. The fluorescence in cells was observed for all the concentrations of FA-CuS NPs that were tested (Results shown only for the 400 µg/mL concentration). By binding fluorescent labels to the FA-CuS NPs, FA-CuS NPs were detected throughout the cytoplasm. The FA-CuS NPs were detected at concentrations as low as 100 µg/mL. This observation suggested that the particles are taken up into SKOV-3 ovarian cells and can be utilized to detect these cells using our PAFC system.

Example 4—Photoacoustic Detection of Cells in Flow

To the best of the inventor's knowledge, this is the first-time ovarian CTCs have been detected by PA in a flow system. The PA flow system consisted of dual syringe pumps simultaneously pumping the sample and air through the system. This created two-phase flow, with alternating sample and air passing through the flow chamber where it was irradiated by NIR light and the PA signal was recorded. To test the ability of the setup to distinguish NP-tagged SKOV-3 cells, four samples were evaluated in our PA flow system: (1) PBS, (2) 100 µg/mL FA-CuS NPs in PBS, (3) SKOV-3 cells tagged with FA-CuS NPs in PBS, (4) SKOV-3 cells alone in PBS at a concentration of 1000 cells per/mL. To ensure that the samples moved uninterrupted through the flow system, 2% TWEEN was added to each of the samples. Higher concentrations of cells were tested, however, this led to inconsistent results. This was attributed to the clogging of the system at high concentrations. For each of the sample conditions, 3 runs lasting 500 acquisitions were recorded. Recordings of the laser and the passage of samples through the flow chamber were collected using a microscope mounted CCD camera (Thorlabs, Austin Tex.). For the cells with NPs, cells alone, PBS, and NPs alone, the amount of total acquisitions examined were 203, 150, 160, and 131 respectively. These resulted indicated the successful detection of ovarian CTCs in flow.

Example 5—Data Analysis of Photoacoustic Detection of Cells in Flow

Figure 5A:
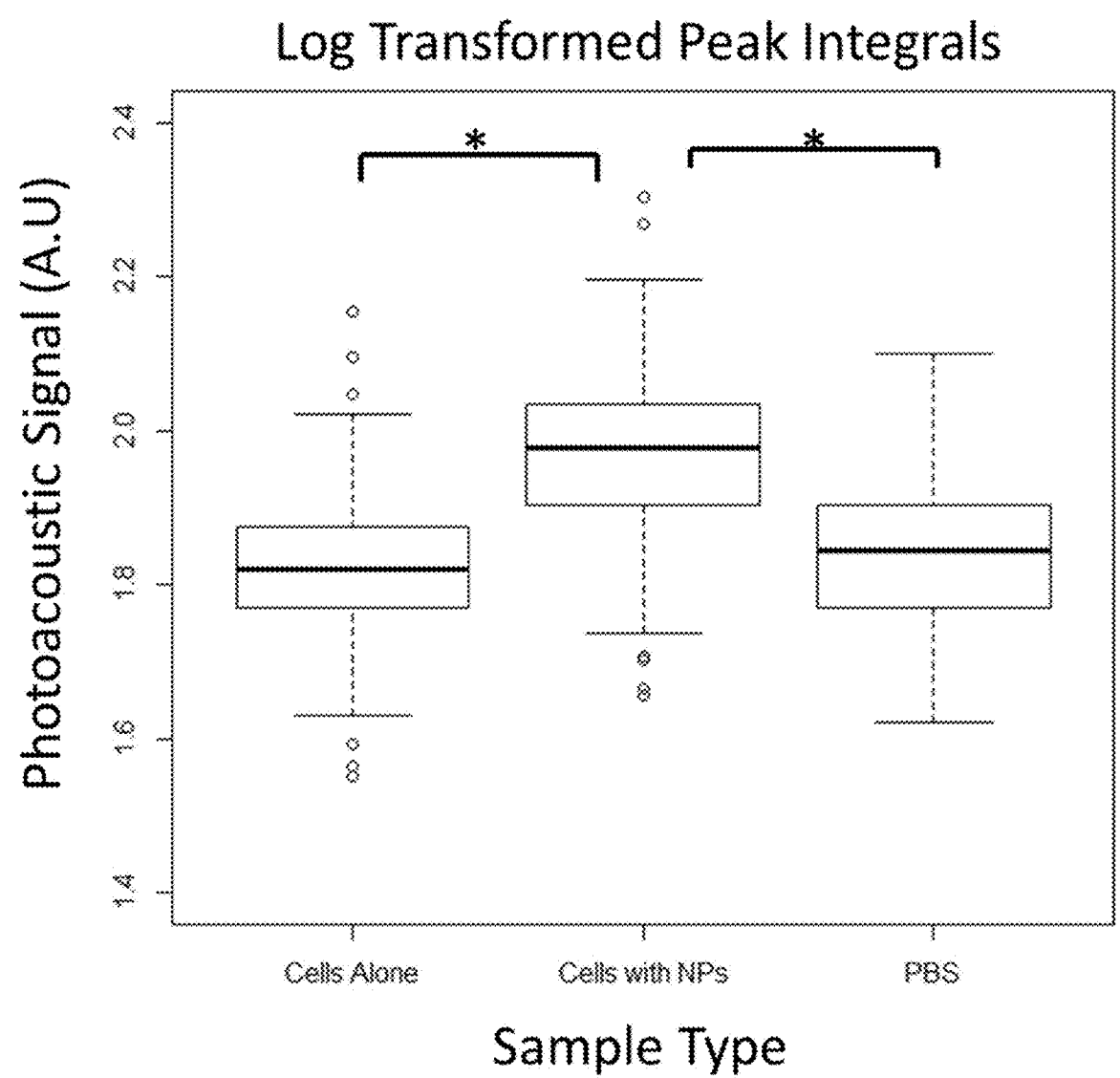
FIGS. 5A-5B show boxplots of the PA signal.
Figure 5B:
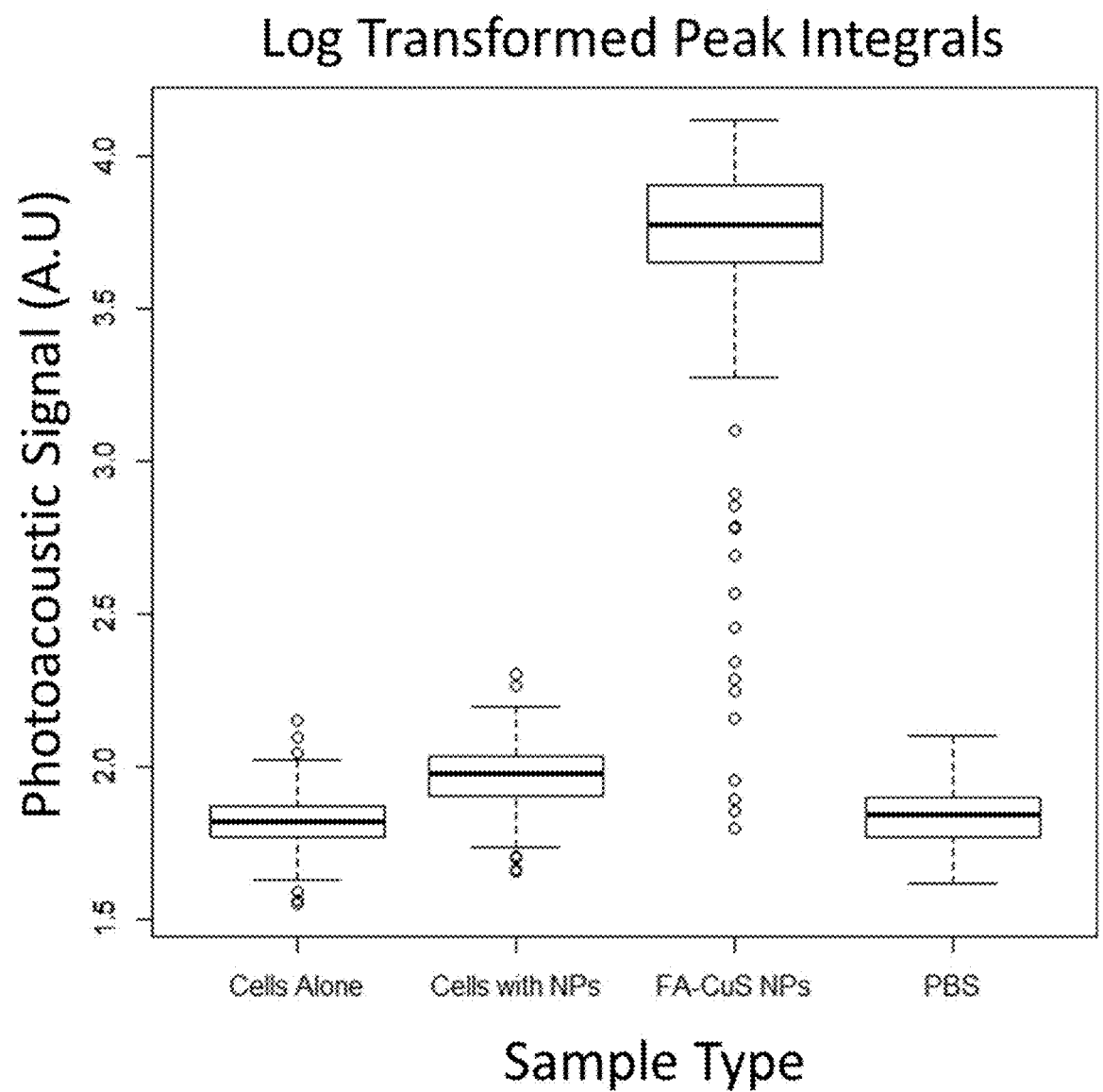

For each acquisition of the PA signal, a Hilbert transform was applied. An analytic signal was then created by combining the data with its own Hilbert transform. The magnitude of the analytic signal was subsequently calculated and integrated to measure the total signal resulting from each acquisition. These values were taken for all samples within each test group. The integrated signals were averaged and compared utilizing a Welch t-test. Representative signals are presented in FIG. 6. At a concentration of 1000 cells/mL, the results showed a significantly higher mean signal in the group of cells that were tagged with FA-CuS NPs ($p<0.05$) than the same concentration of cells that had not been incubated with NPs. In addition, when concentrations of cells were analyzed in the system that had not been tagged by NPs, the PA signal was not significantly different than PBS alone ($p<0.05$). The box plots of these signals are displayed in FIG. 5. The successful identification of ovarian CTCs in flow provides insights into future in vivo and in vitro applications of PAFC. The concentration of 100 µg/mL FA-CuS NPs produced a significant PA signal. Image reconstructions of the signal are presented in FIG. 7. The results clearly indicated the capacity to detect ovarian CTCs by utilizing FA-CuS NPs in the custom flow system.

Example 6—Silver Glutathione Nanoparticles as contrast agents

Figure 8:
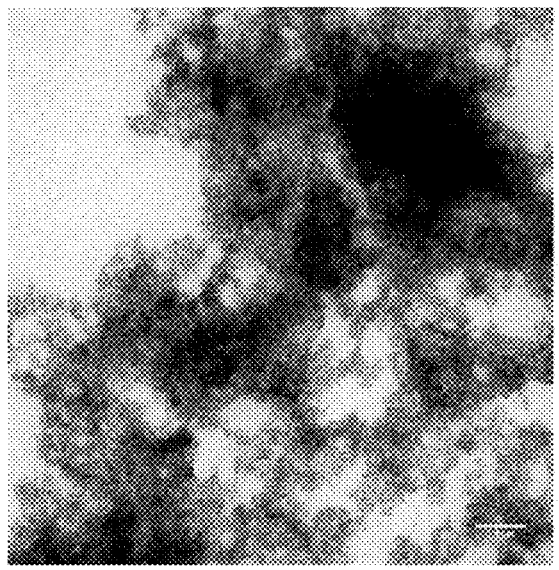
FIG. 8 show silver glutathione nanoparticles synthesis. Silver glutathione nanoparticles were synthesized by combining glutathione and silver nitrate and stirring over a period of 7 days at 60° C. TEM images show the increasing diameter of silver nanoparticles over time.
Figure 8:
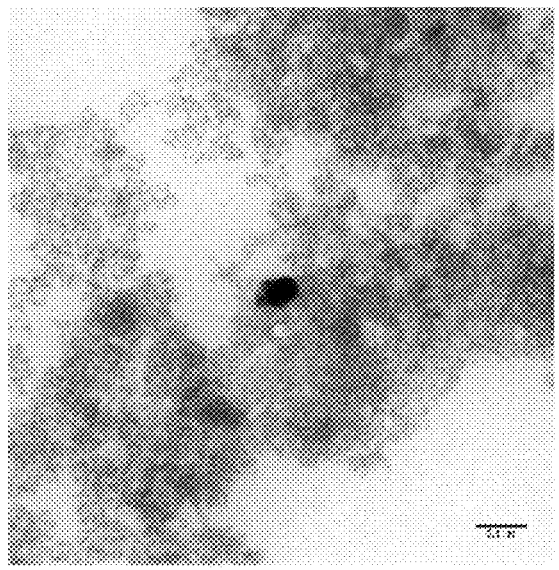
Figure 8:
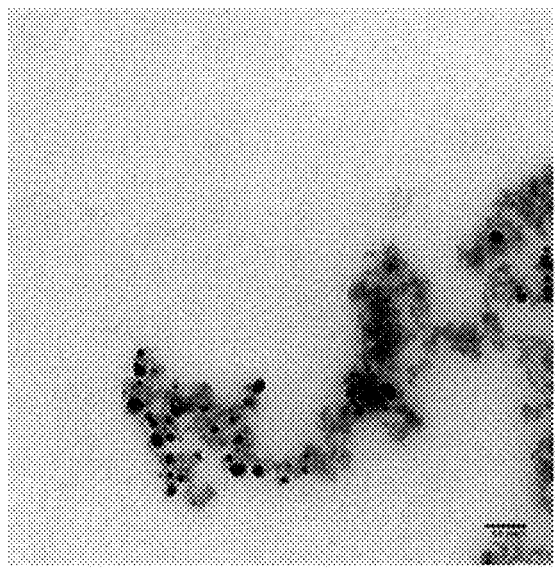
Figure 8:
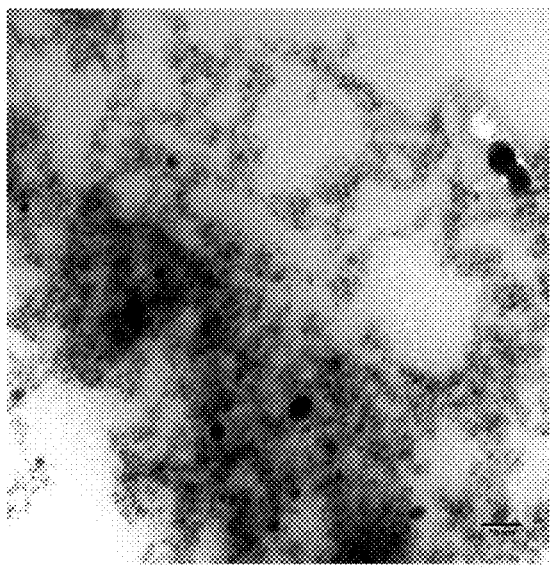
Figure 9:
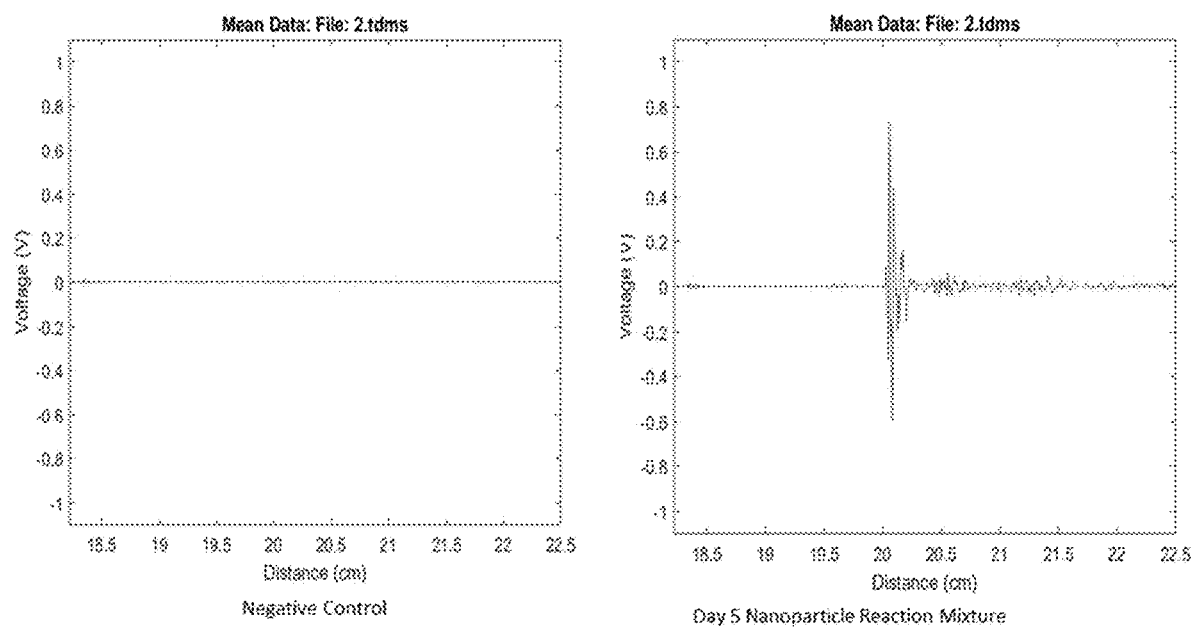
FIG. 9 show the photoacoustic signal generation of silver glutathione nanoparticles. Photoacoustic signal generation of the silver glutathione nanoparticle reaction mixtures were tested by firing a laser at vial containing the nanoparticles and an ultrasound transducer. Initial testing of the reaction mixtures showed the generation of a photoacoustic signal at 432 nm.
Figure 10:
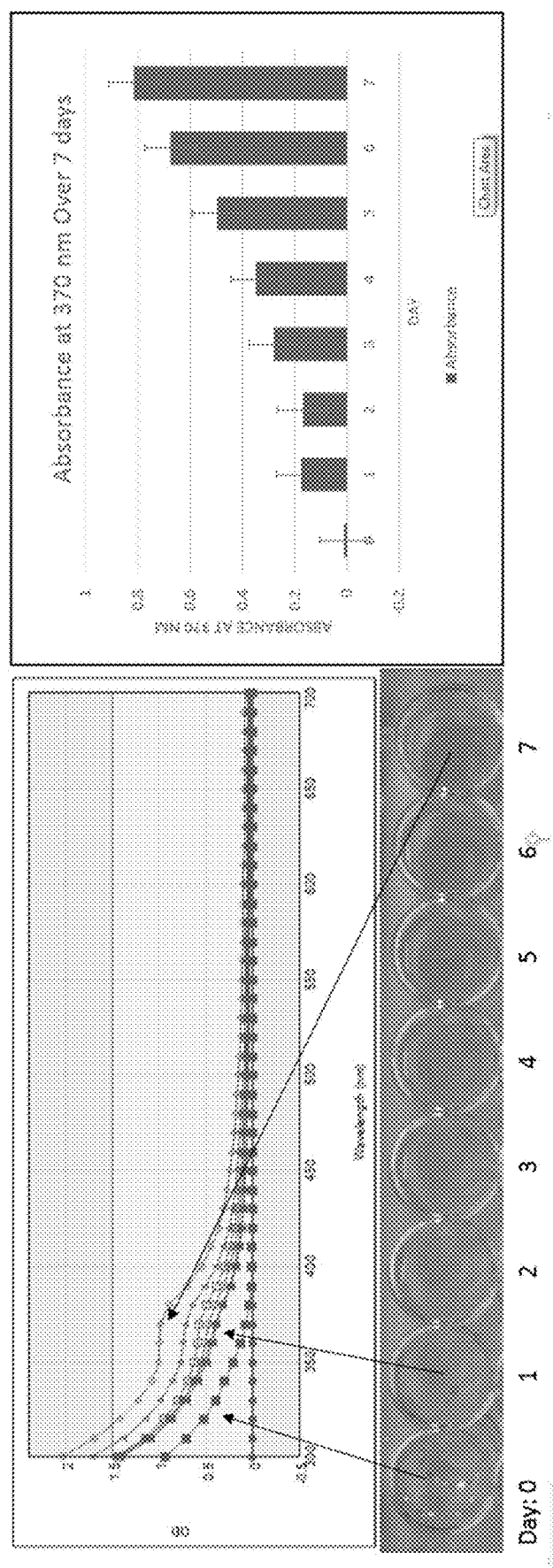
FIG. 10 shows the characterization of silver glutathione nanoparticles. Increased absorbance at 370 nm indicated the growth of the nanoparticles. A gradual increase in color from clear to dark yellow over the course of the reaction also indicated the presence of newly synthesized silver glutathione nanoparticles.
Figure 11A:
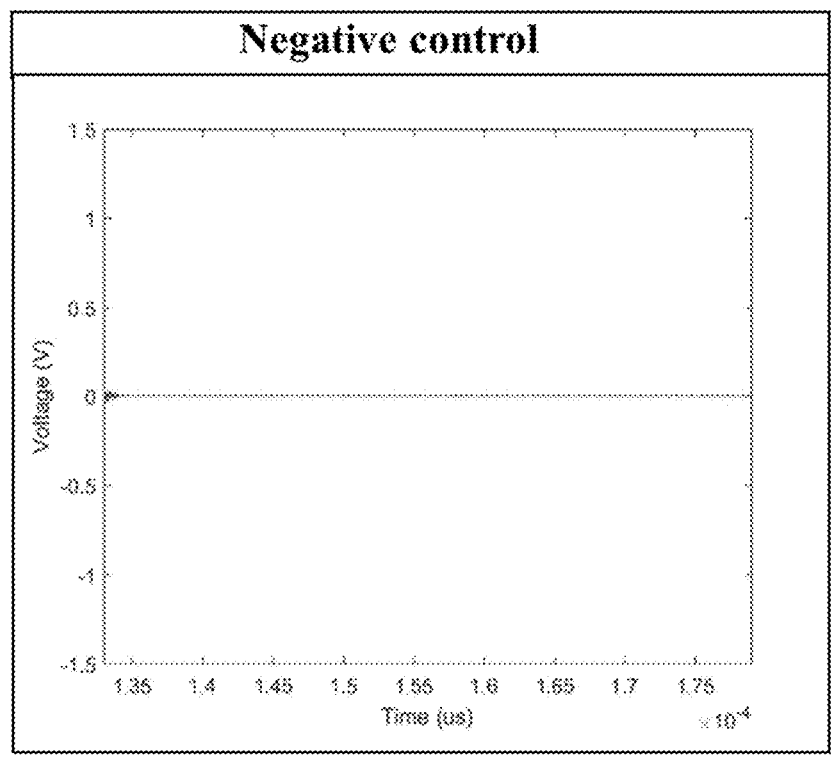
FIGS. 11A-11C show the photoacoustic signal generation of a negative control (FIG. 11A), a positive control (FIG. 11B) and silver glutathione nanoparticles from day 5 (FIG. 11C). The synthesized particles produce a photoacoustic effect when exposed to 390 nm laser pulses.
Figure 11B:
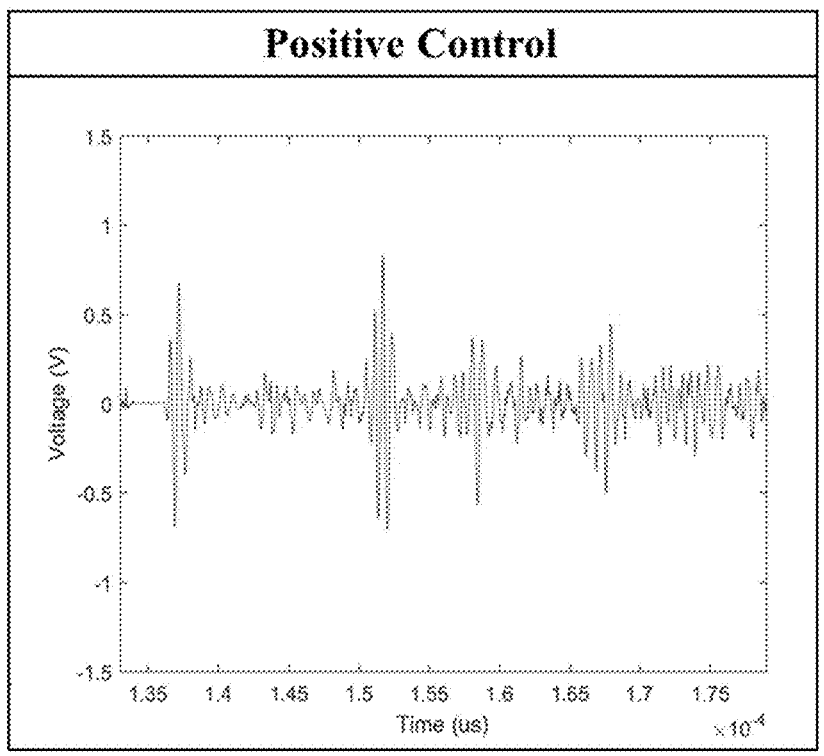
Figure 11C:
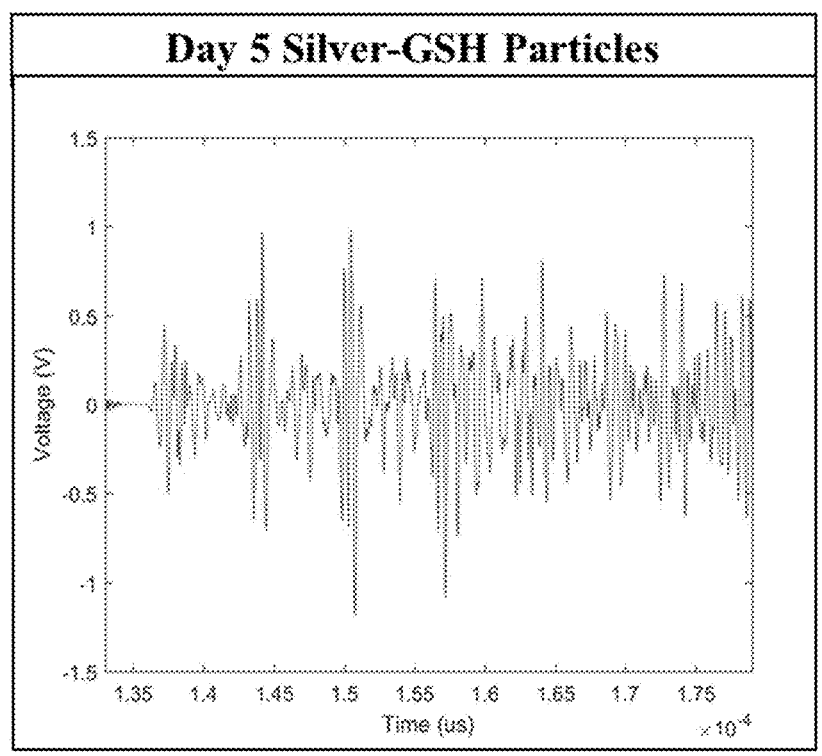
Figure 12A:
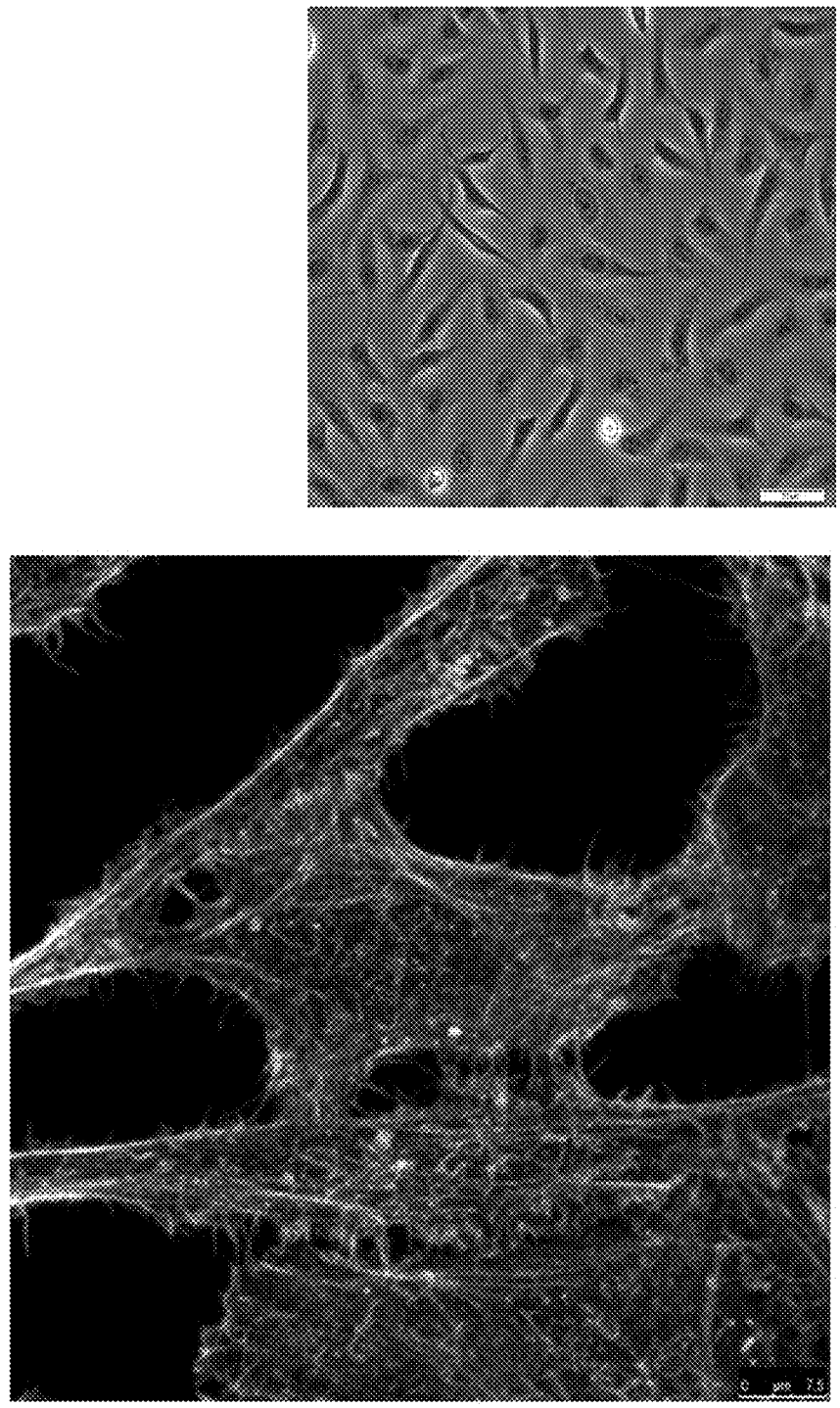
FIGS. 12A-12E show the uptake of silver glutathione nanoparticles by cancer cells. Varying concentrations of synthesized day 5 nanoparticles were applied to cell culture, and incubated for 24 hours. The cells were then imaged by confocal and phase microscopy. Nanoparticles within cells were imaged using reflection microscopy and are represented by green. The resulting images show concentration dependent uptake of nanoparticles into cervical cancer cells and dispersion of the nanoparticles throughout the cytoplasm (circled) for the negative control (FIG. 12A), a positive control (FIG. 12B), silver-glutathione nanoparticles at 3 μg/mL (FIG. 12C), silver-glutathione nanoparticles at 40 μg/mL (FIG. 12D), and silver-glutathione nanoparticles at 80 μg/mL (FIG. 12E).
Figure 12B:
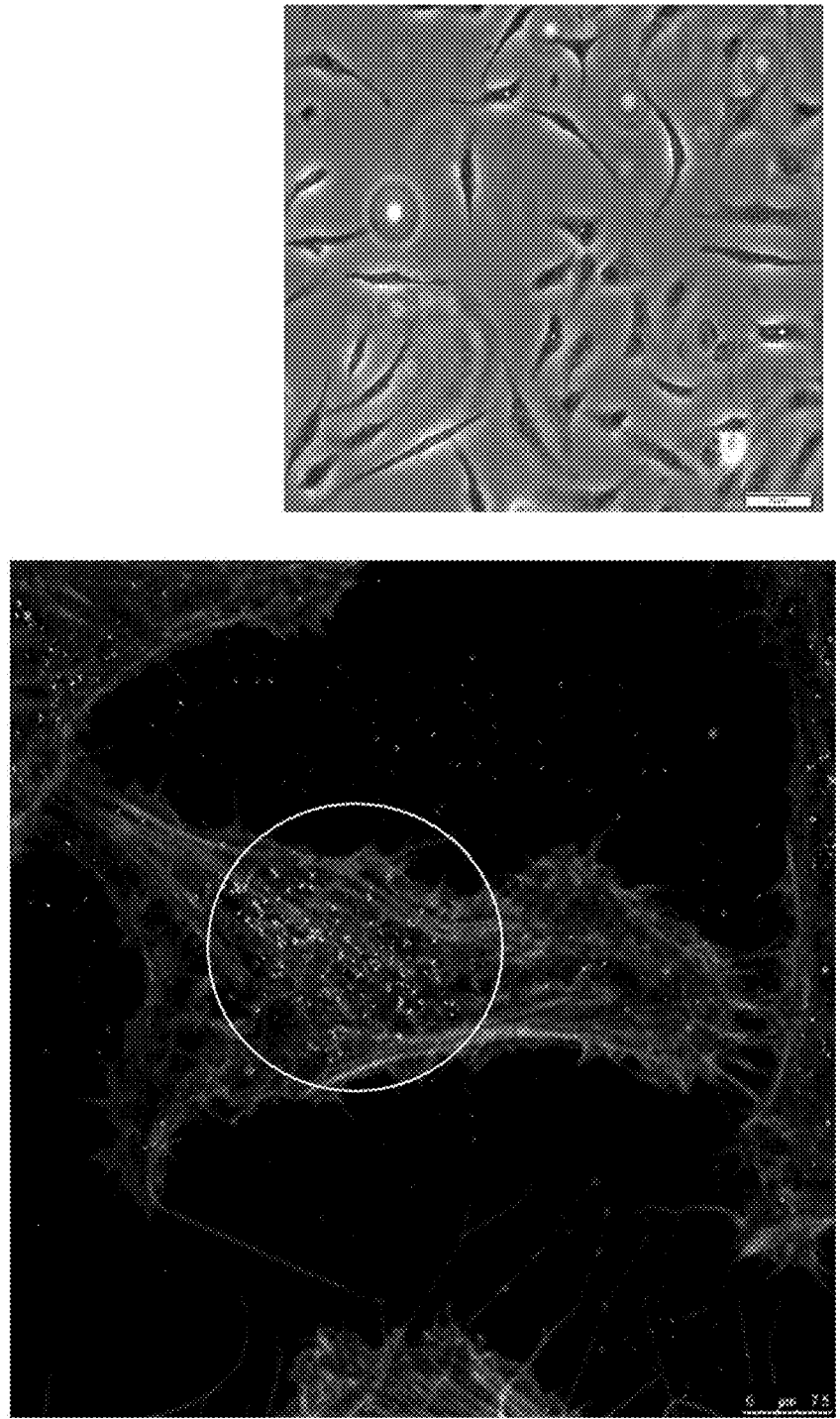
Figure 12C:
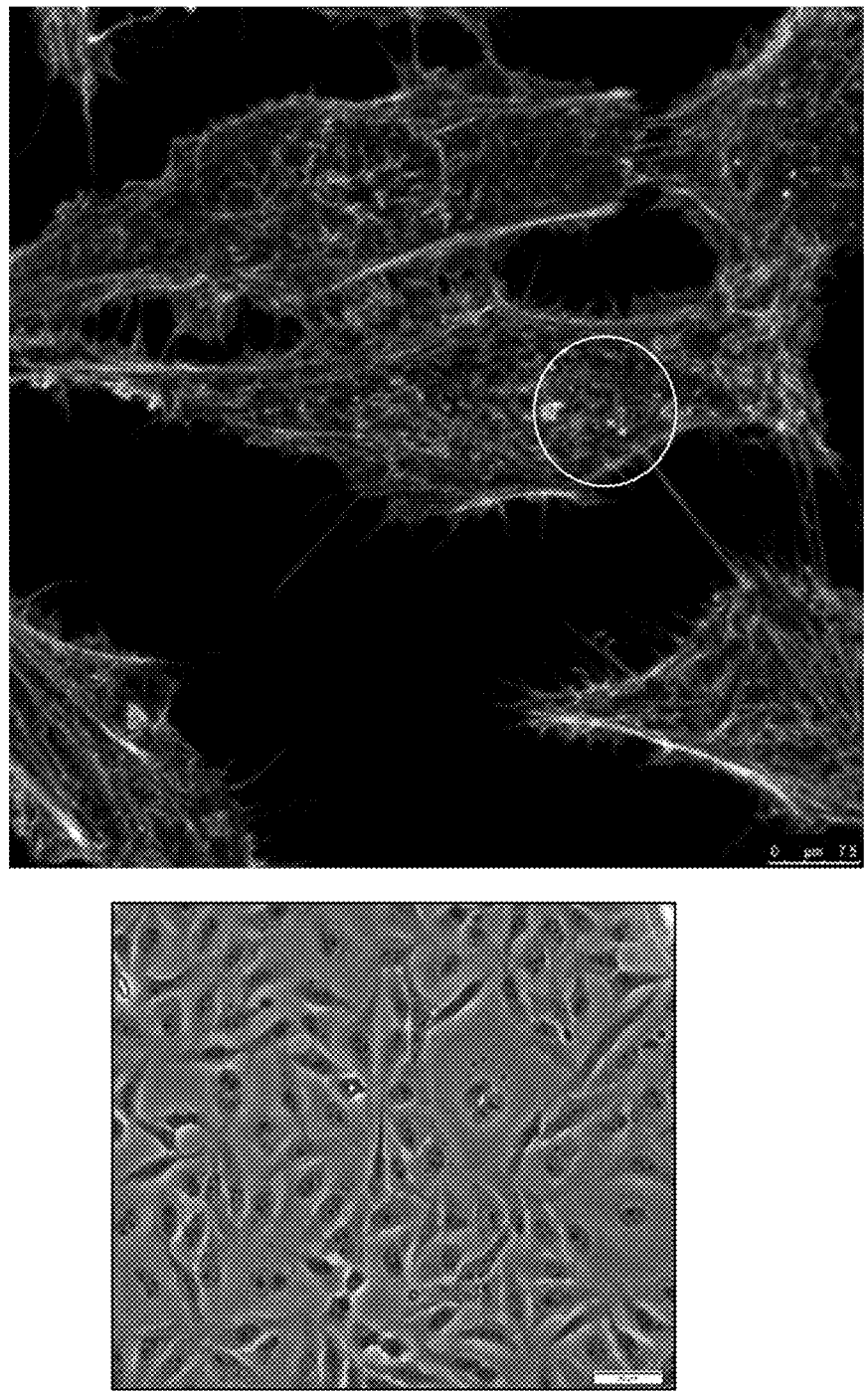
Figure 12D:
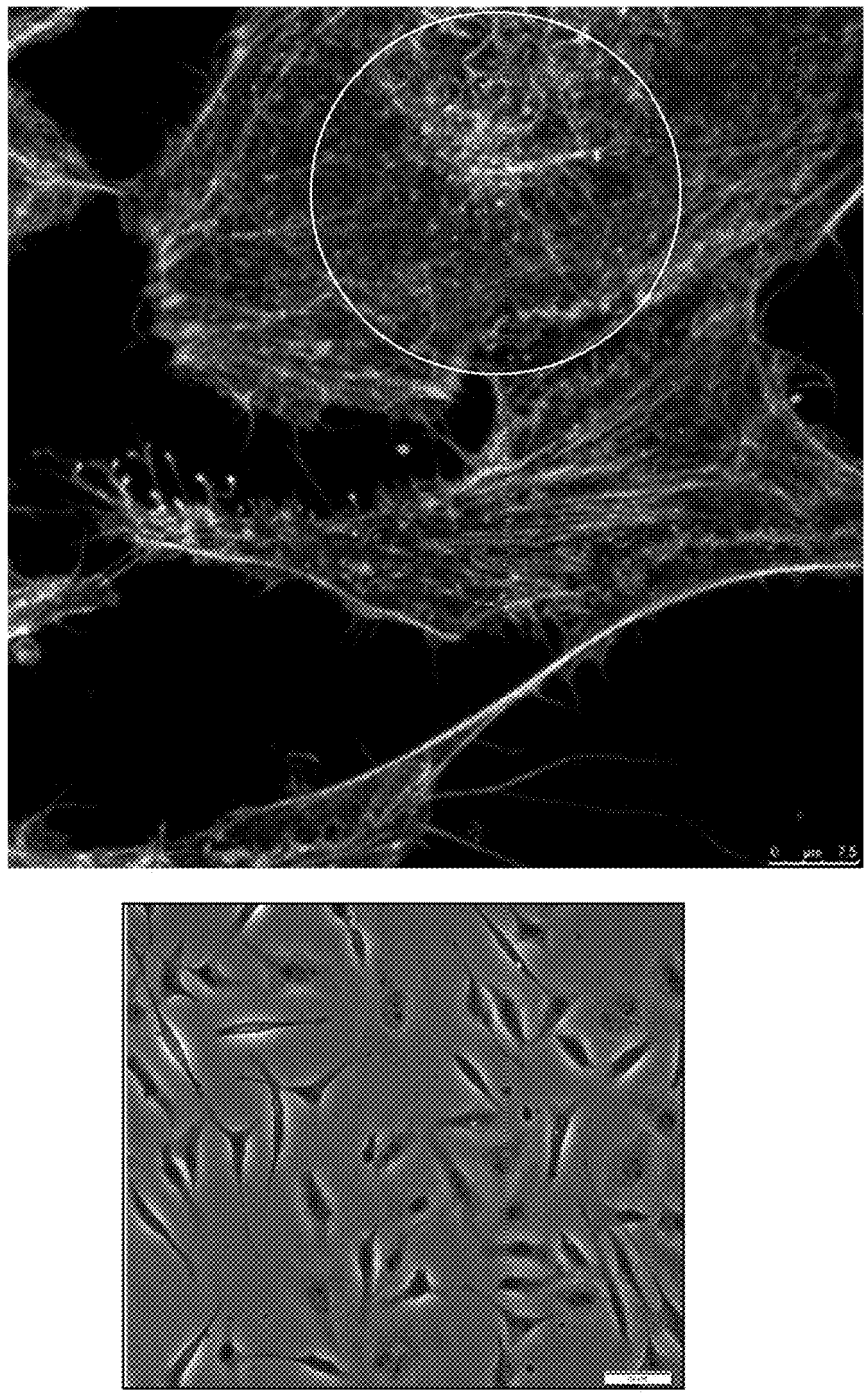
Figure 12E:
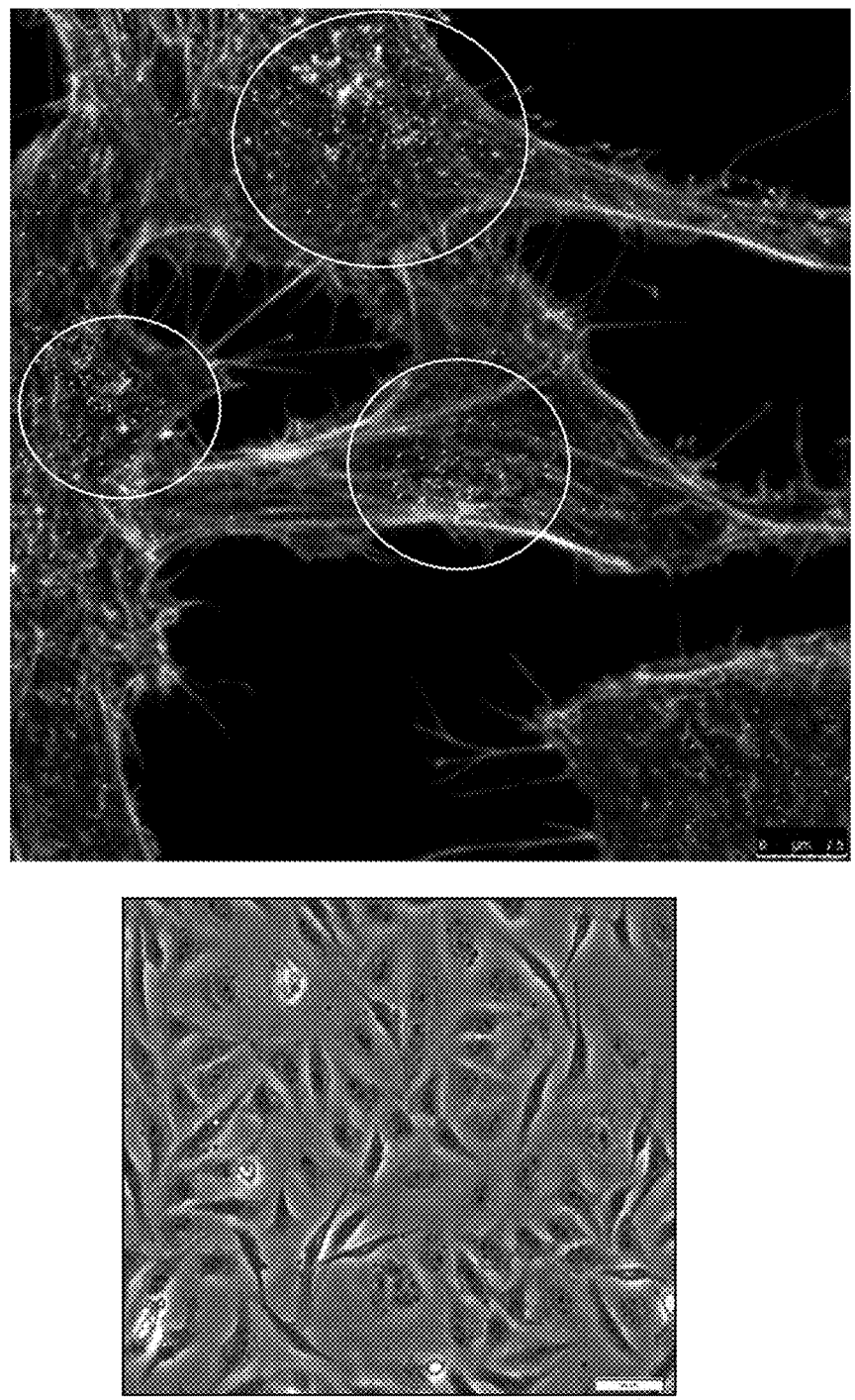

Silver nanoparticles produced by green methods can act as contrast agents and photothermal targets for PAI. The expanding diameter of SNP's over the 7-day reaction period was observed by TEM (FIG. 8) and corresponded with a growing absorbance peak at 370 nm when analyzed with UV-Vis spectroscopy (FIG. 10). Initial testing showed the reaction mixtures generated a photoacoustic signal at 432 nm (FIG. 9) and the synthesized particles produced a photoacoustic effect when exposed to 390 nm laser pulses.

Figure 14A:
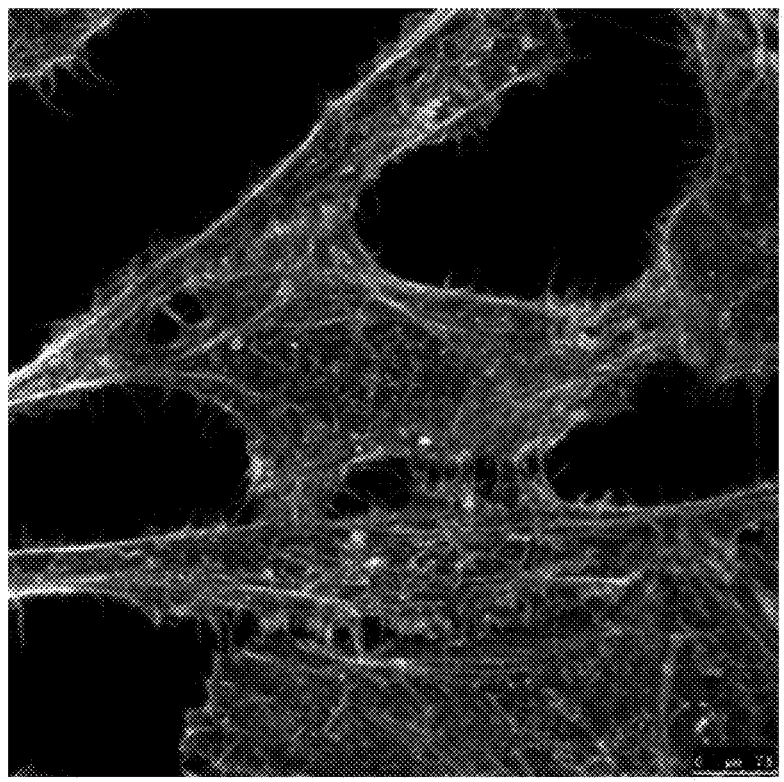
FIGS. 14A-14D show the silver glutathione nanoparticle (SNP) contrast agents.
Figure 14B:
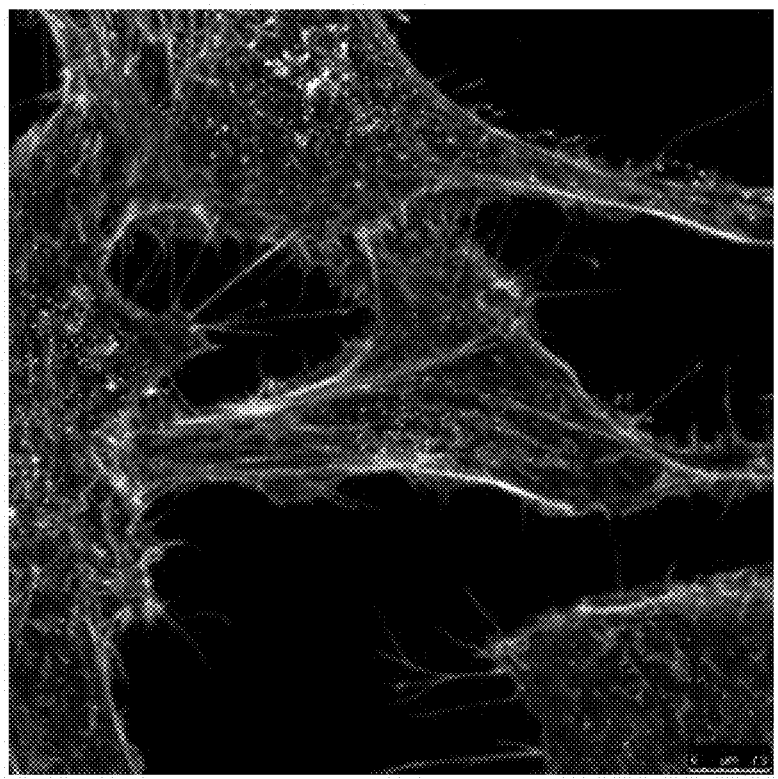
Figure 14C:
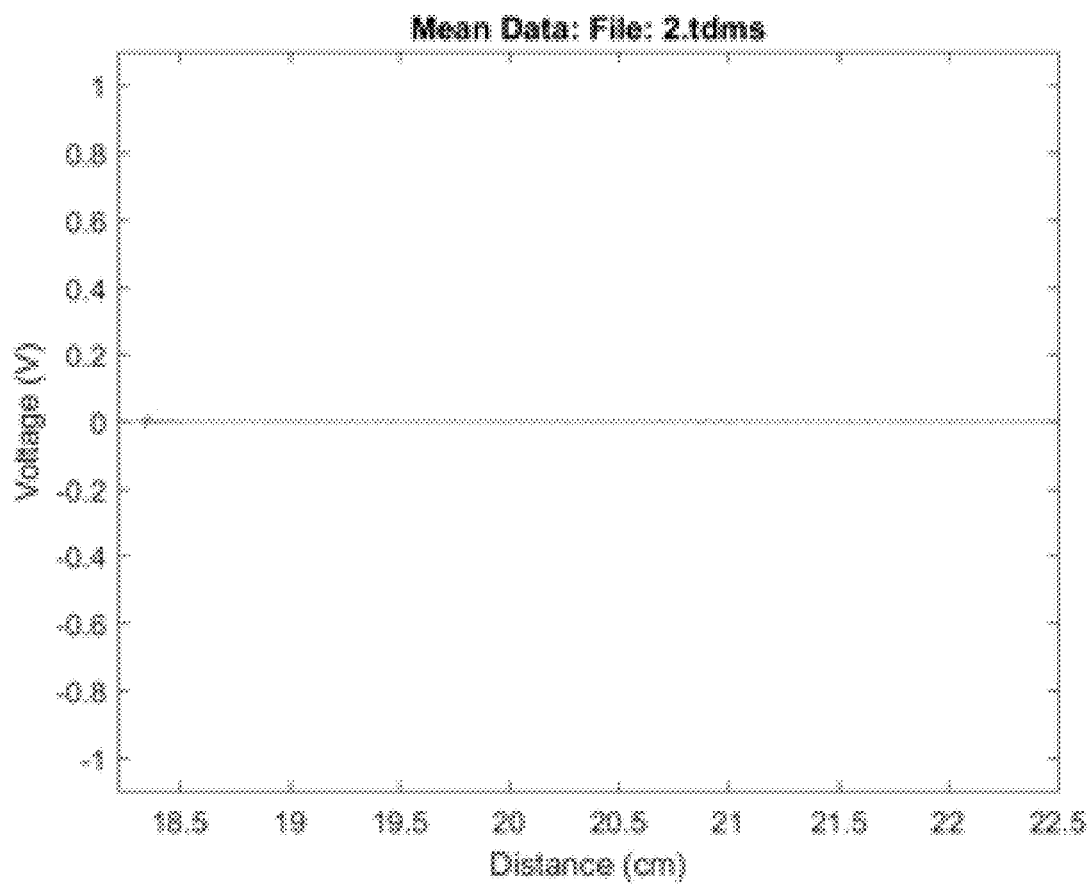
Figure 14D:
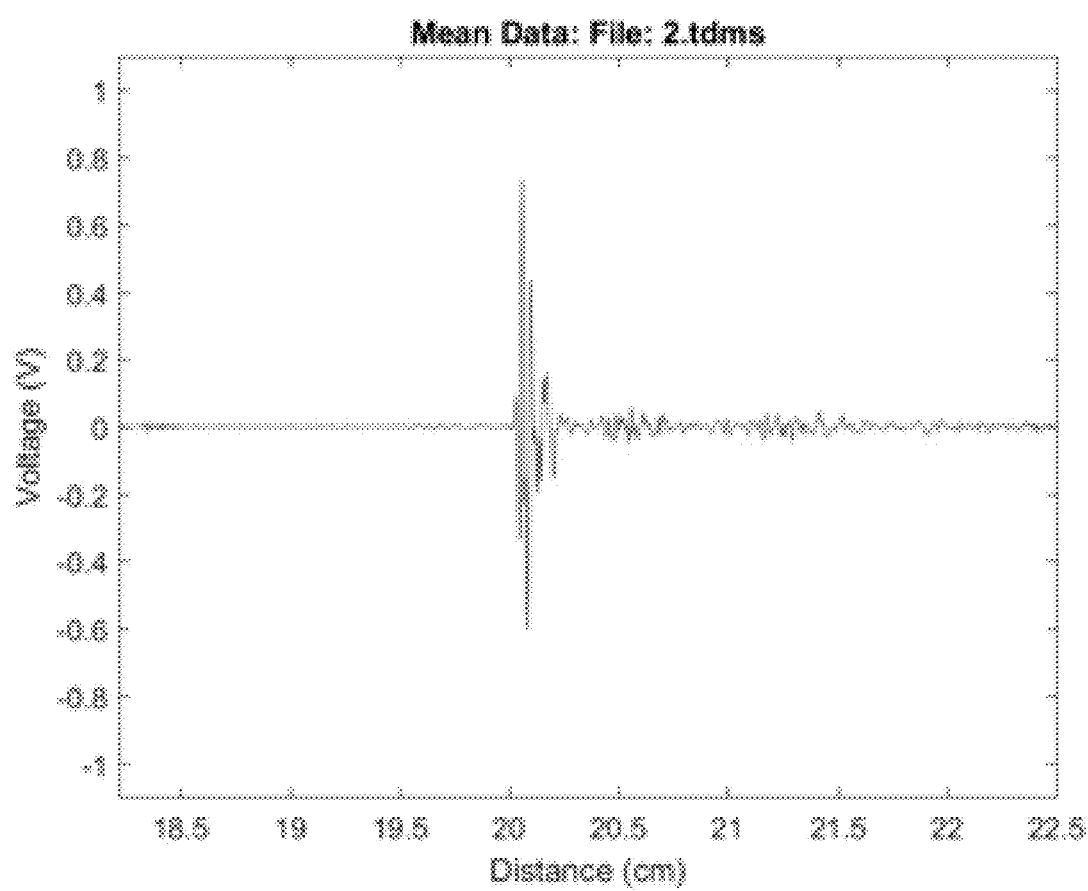

Increasing concentrations of SNPs inside of cells were shown in cell cultures up to 80 µg/mL using confocal microscopy (FIGS. 14A-14B). Cells were imaged by light field microscopy, and cytotoxicity was observed at a concentration of 160 µg/mL. SNPs demonstrated generation of a photoacoustic effect when stimulated at 432 nm using an Nd/Yag Sapphire laser (FIGS. 14C-14D).

Varying concentrations of synthesized day 5 nanoparticles showed concentration dependent uptake of nanoparticles into cervical cancer cells with dispersion throughout the cytoplasm (FIGS. 12A-12E).

These results show the ability of glutathione coated silver nanoparticles to act as contrast agents for PAI in cancer culture. These photoacoustic contrast agents may act as photothermal probes, and can be imaged ex-vivo by fluorescence microscopy. The nanoparticle system may be used to address the need for higher specificity and sensitivity for point of care diagnosis of ovarian cancer, while simultaneously acting as a guide for photothermal ablation therapy.

Figure 13A:
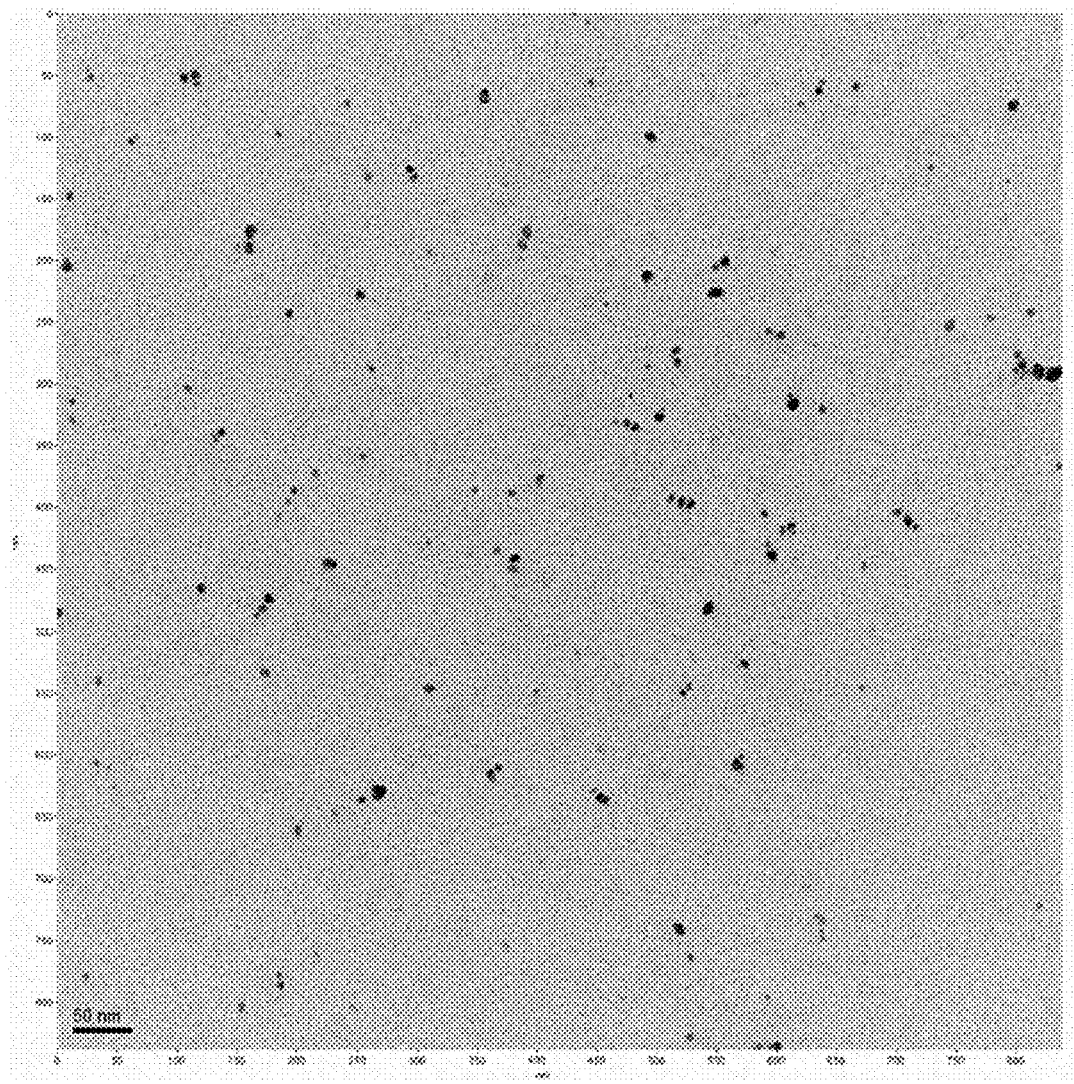
FIGS. 13A-13B show folate capped copper sulfide nanoparticles.
Figure 13B:
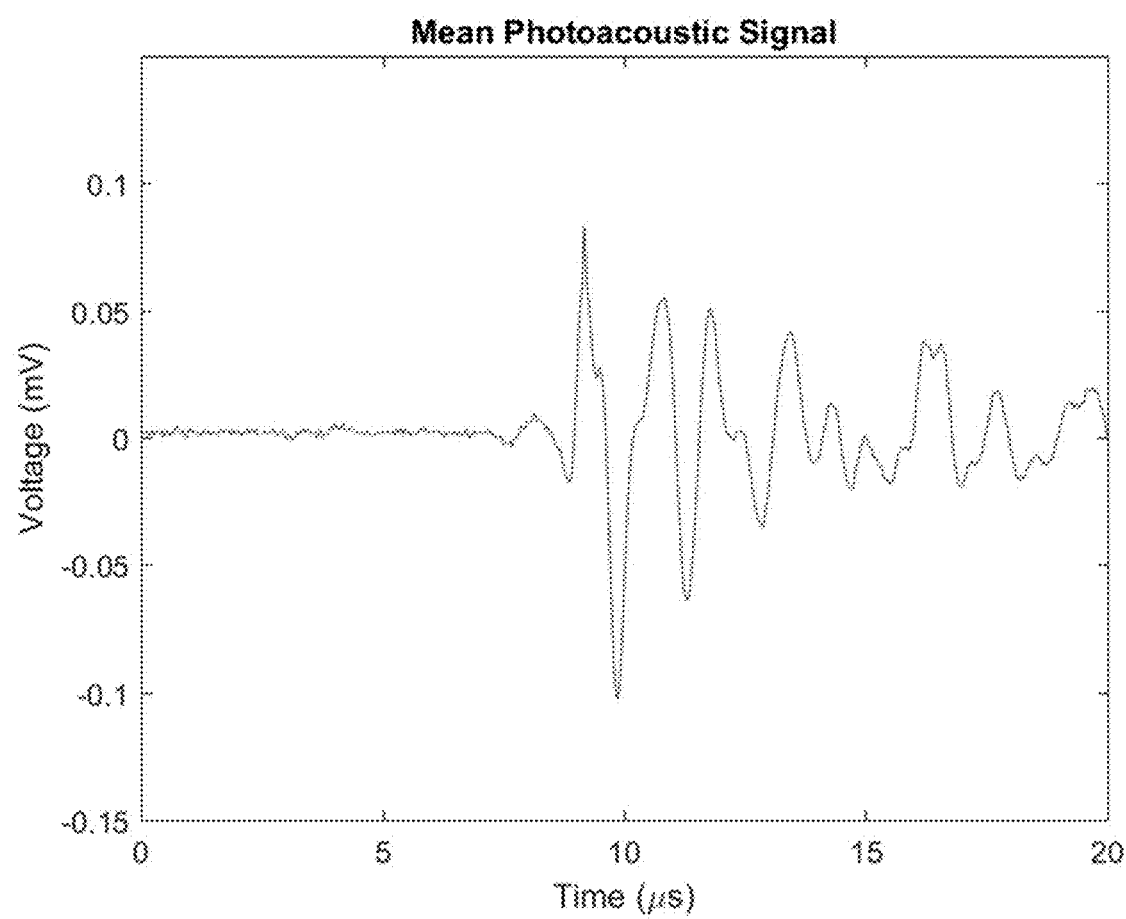

Because glutathione conjugated silver nanoparticles can be biosynthesized by cells and form larger silver aggregates this nanoparticle system may be used to characterize the changing nature of these agents within cells by photo acoustics and light microscopy. Other nanomaterials, such as folate capped copper sulfide nanoparticles (FIG. 13A-13B)

may be used in conjunction with our silver glutathione system to accomplish a multiplexed nanoparticle system that can improve the sensitivity and specificity of the detection of ovarian cancer.

For reasons of completeness, various aspects of the invention are set out in the following numbered clauses:

Clause 1. A method of detecting an ovarian circulating tumor cell in a subject suspected of having cancer, the method comprising: obtaining a test sample from the subject; contacting the test sample with a nanoparticle, wherein the nanoparticle is configured for uptake by an ovarian circulating tumor cell; optionally incubating the test sample with the nanoparticle for a period of time sufficient to allow an ovarian circulating tumor cell in the test sample to uptake the nanoparticle; removing from the test sample any free nanoparticle not taken up by an ovarian circulating tumor cell; illuminating the test sample with laser light; and detecting the presence of the ovarian circulating tumor cell in the subject when a photoacoustic signal generated by the nanoparticle is detected with an acoustic sensor.

Clause 2. The method of clause 1, wherein the free nanoparticle is removed from the test sample by washing the test sample or centrifuging the test sample.

Clause 3. The method of clause 1 or 2, wherein the test sample comprises intraperitoneal fluid or peripheral blood.

Clause 4. The method of any of clauses 1-3, wherein the test sample is incubated with the nanoparticle for about 1 hour to about 5 hours.

Clause 5. The method of any of clauses 1-4, wherein the test sample is contacted with the nanoparticle for about 2 hours.

Clause 6. The method of any of clauses 1-5, wherein the nanoparticle comprises copper sulfide.

Clause 7. The method of any of clauses 1-6, wherein the nanoparticle is functionalized with folic acid.

Clause 8. The method of any of clauses 1-7, wherein the nanoparticle comprises a fluorescent label.

Clause 9. The method of clause 8, wherein the fluorescent label is Texas Red™.

Clause 10. The method of any of clauses 1-9, wherein the nanoparticle has a diameter of about 3 nm to about 20 nm.

Clause 11. The method of any of clauses 1-10, wherein the nanoparticle has a diameter of about 9 nm.

Clause 12. The method of any of clauses 1-11, wherein the nanoparticle has a hydrodynamic diameter of about 50 nm to about 125 nm.

Clause 13. The method of any of clauses 1-12, wherein the nanoparticle has a hydrodynamic diameter of about 74 nm.

Clause 14. The method of any of clauses 1-13, wherein the laser light has a wavelength between 700 and 1400 nm.

Clause 15. The method of any of clauses 1-14, wherein the laser light has a wavelength between 950 and 1150 nm.

Clause 16. The method of any of clauses 1-15, wherein the laser light has a wavelength of about 1050 nm.

Clause 17. The method of any of clauses 1-16, further comprising circulating the test sample through a capillary tube in a test chamber filled with water.

Clause 18. The method of clause 1-17, further comprising alternating air and the test sample through the capillary tube.

Clause 19. The method of any of clauses 1-18, further comprising imaging the test sample.

Clause 20. The method of any of clauses 1-19, further comprising incubating the test sample with a marker, wherein the marker is configured to identify a cell population or a subset thereof in the test sample.

Clause 21. The method of clause 20, wherein the marker comprises a tag.

Clause 22. The method of clause 20 or 21, wherein the marker comprises a second nanoparticle.

Clause 23. The method any of clauses 20-22, wherein the marker comprises a second nanoparticle that is configured for uptake by a cancer cell.

Clause 24. The method any of clauses 20-23, wherein the marker comprises a silver nitrate nanoparticle.

Clause 25. The method of any of clauses 20-24, wherein the marker comprises a nanoparticle functionalized with glutathione.

Clause 26. The method of clause 25, further comprising illuminating the test sample with laser light at a wavelength between about 350 nm and about 650 nm.

Clause 27. The method of clause 26, wherein the laser light is at a wavelength between about 350 nm and about 500 nm.

Clause 28. The method of any one of clauses 26 or 27, wherein the laser light is at a wavelength of about 430 nm.

Clause 29. The method of any of clauses 1-28, wherein the presence of circulating ovarian tumor cells in the test sample indicates presence of metastatic ovarian cancer in the subject.

Clause 30. A method of detecting the presence of metastatic ovarian cancer in a subject, the method comprising: obtaining a test sample from the subject; contacting the test sample with a nanoparticle, wherein the nanoparticle is configured for uptake by an ovarian circulating tumor cell; optionally incubating the test sample with the nanoparticle for a period of time sufficient to allow an ovarian circulating tumor cell in the test sample to uptake the nanoparticle; removing from the test sample any free nanoparticle not taken up by an ovarian circulating tumor cell; illuminating the test sample with laser light; and detecting the presence of metastatic ovarian cancer in the subject when a photoacoustic signal generated by the nanoparticle is detected with an acoustic sensor.

Clause 31. A photoacoustic flow system comprising: a flow chamber configured to support a capillary tube, the flow chamber including a window and a slot; a pump system coupled to the capillary tube, the pump system including a first syringe pump filled with air and a second syringe pump containing a sample, wherein the first pump injects the air into the capillary tube, and the second pump injects the sample into the capillary tube to produce two-phase flow with alternating air and sample through the capillary tube; an optical fiber coupled to a laser and configured to transmit light to excite the sample in the capillary tube; an ultrasound transducer coupled to the window in the flow chamber, wherein the ultrasound transducer detects acoustic signals generated by excitation of the sample; an inverted fluorescence microscope including a stage for supporting the flow chamber and a camera aligned with the slot in the flow chamber for imaging the sample as it passes through the capillary tube; and a data acquisition system configured to receive the acoustic signals from the ultrasound transducer and the images from the camera to reconstruct and display a photoacoustic image of the sample.

Clause 32. The photoacoustic flow system of clause 31, further comprising an ultrasound pulser/receiver coupled to the ultrasound transducer and configured to receive and amplify the acoustic signals.

Clause 33. The photoacoustic flow system of clause 31, wherein the window and the slot are oriented in the flow chamber to provide alignment of the ultrasound transducer and the light from the optical fiber.

Clause 34. The photoacoustic flow system of clause 31, wherein the window is oriented perpendicular to a longitudinal axis defined by the capillary tube.

Various features and advantages of the invention are set forth in the following claims.

What is claimed is:

1. A method of detecting ovarian circulating tumor cells in a subject suspected of having cancer, the method comprising:
   obtaining a test sample from the subject;
   contacting the test sample with nanoparticles, wherein the nanoparticles are folic acid functionalized nanoparticles further comprising a fluorescent label;
   incubating the test sample with the nanoparticles for a period of time sufficient to allow uptake of the nanoparticles by the ovarian circulating tumor cells in the test sample;
   removing from the test sample any free nanoparticles not taken up by an ovarian circulating tumor cell;
   illuminating the test sample with laser light to excite the test sample in the capillary tube; and
   detecting the presence of the ovarian circulating tumor cells in the subject's sample when photoacoustic signals generated by the nanoparticles are detected by displaying the photoacoustic signals as a photoacoustic image;
   wherein the method is performed using a photoacoustic flow system comprising:
   a flow chamber configured to support a capillary tube, the flow chamber including a window and a slot;
   a pump system coupled to the capillary tube, the pump system including a first syringe pump filled with air and a second syringe pump containing the test sample, wherein the first pump injects the air into the capillary tube, and the second pump injects the test sample into the capillary tube to produce two-phase flow with alternating air and test sample through the capillary tube;
   an optical fiber coupled to a laser and configured to transmit the laser light that excites the nanoparticles uptaken by the ovarian circulating tumor cells in the test sample in the capillary tube;
   an ultrasound transducer coupled to the window of the flow chamber, wherein the ultrasound transducer detects the photoacoustic signals generated by the excited nanoparticles;
   an inverted fluorescence microscope including a stage for supporting the flow chamber and a camera aligned with the slot of the flow chamber for obtaining images of the test sample as it passes through the capillary tube; and
   a data acquisition system configured to receive the photoacoustic signals from the ultrasound transducer and the images from the camera to reconstruct and display the photoacoustic image.

2. The method of claim 1, wherein free nanoparticles are removed from the test sample by washing the test sample or centrifuging the test sample.

3. The method of claim 1, wherein the test sample comprises intraperitoneal fluid or peripheral blood.

4. The method of claim 1, wherein the test sample is incubated with the nanoparticles for 1 hour to 5 hours.

5. The method of claim 4, wherein the test sample is contacted with the nanoparticles for 2 hours.

6. The method of claim 1, wherein the nanoparticles are copper sulfide nanoparticles.

7. The method of claim 1, wherein the fluorescent label is sulforhodamine 101 acid chloride.

8. The method of claim 1, wherein the nanoparticle has a diameter of 3 nm to 20 nm.

9. The method of claim 8, wherein the nanoparticle has a diameter of 9 nm.

10. The method of claim 1, wherein an aggregate of nanoparticles has a hydrodynamic diameter of 50 nm to 125 nm, as measured by dynamic light scattering (DLS).

11. The method of claim 10, wherein the aggregate of nanoparticles has a hydrodynamic diameter of 74 nm.

12. The method of claim 1, wherein the laser light has a wavelength between 700 and 1400 nm.

13. The method of claim 12, wherein the laser light has a wavelength between 950 and 1150 nm.

14. The method of claim 12, wherein the laser light has a wavelength of 1050 nm.

15. The method of claim 1, further comprising circulating the test sample through the capillary tube in the flow chamber, wherein the flow chamber is filled with water.

16. The method of claim 15, wherein circulating the test sample through the capillary tube comprises alternating air and test sample through the capillary tube.

17. The method of claim 1, further comprising obtaining images of the test sample with the camera.

18. The method of claim 1, further comprising incubating the test sample with a marker, wherein the marker is configured to identify a cell population or a subset thereof in the test sample.

19. The method of claim 18, wherein the marker comprises a tag.

20. The method of claim 18, wherein the marker comprises a second nanoparticle different from the folic acid functionalized nanoparticles.

21. The method of claim 18, wherein the marker comprises a second nanoparticle that is a glutathione functionalized silver nitrate nanoparticle that is uptaken by a cancer cell.

22. The method of claim 21, further comprising an additional illuminating step, wherein the additional illuminating step comprises illuminating the test sample with laser light at a wavelength between 350 nm and 650 nm.

23. The method of claim 22, wherein the laser light is at a wavelength between 350 nm and 500 nm.

24. The method of claim 22, wherein the laser light is at a wavelength of 430 nm.

* * * * *